United States Patent
Hodes et al.

(10) Patent No.: US 12,357,549 B2
(45) Date of Patent: Jul. 15, 2025

(54) METHOD FOR DYEING KERATINOUS MATERIAL, COMPRISING THE USE OF AN ORGANOSILICON COMPOUND, A DYEING COMPOUND, A SEALING REAGENT, AND A PRE-TREATMENT AGENT

(71) Applicant: Henkel AG & Co. KGaA, Duesseldorf (DE)

(72) Inventors: Jing Hodes, Hagen (DE); Gabriele Weser, Essen (DE); Ulrike Schumacher, Duesseldorf (DE); Claudia Kolonko, Remscheid (DE); Caroline Kriener, Duesseldorf (DE)

(73) Assignee: Henkel AG & Co. KGaA, Düesseldorf (DE)

( * ) Notice: Subject to any disclaimer, the term of this patent is extended or adjusted under 35 U.S.C. 154(b) by 87 days.

(21) Appl. No.: 18/279,885

(22) PCT Filed: Jan. 17, 2022

(86) PCT No.: PCT/EP2022/050857
§ 371 (c)(1),
(2) Date: Sep. 1, 2023

(87) PCT Pub. No.: WO2022/184337
PCT Pub. Date: Sep. 9, 2022

(65) Prior Publication Data
US 2024/0173222 A1 May 30, 2024

(30) Foreign Application Priority Data
Mar. 3, 2021 (DE) .................. 10 2021 202 048.8

(51) Int. Cl.
*A61Q 5/10* (2006.01)
*A61K 8/22* (2006.01)
*A61Q 5/06* (2006.01)

(52) U.S. Cl.
CPC ............ *A61K 8/22* (2013.01); *A61Q 5/065* (2013.01); *A61K 2800/432* (2013.01); *A61K 2800/596* (2013.01); *A61K 2800/88* (2013.01)

(58) Field of Classification Search
CPC ............ A61K 8/22; A61K 2800/432; A61K 2800/596; A61K 2800/88; A61K 8/585; A61K 8/8141; A61K 8/893; A61K 8/894; A61K 8/898; A61Q 5/065; A61Q 5/10
USPC ............................................................. 8/405
See application file for complete search history.

(56) References Cited

U.S. PATENT DOCUMENTS

| 7,806,941 | B2 | 10/2010 | Brun et al. | |
|---|---|---|---|---|
| 11,291,622 | B2 | 4/2022 | Lechner et al. | |
| 2010/0083446 | A1* | 4/2010 | Brun | A61K 8/891 8/405 |
| 2015/0080338 | A1* | 3/2015 | Lorant | A61K 8/8152 514/63 |
| 2019/0143150 | A1* | 5/2019 | Dähne | A61Q 5/065 424/70.6 |
| 2022/0000749 | A1 | 1/2022 | Weser et al. | |
| 2022/0054394 | A1 | 2/2022 | Schoepgens et al. | |
| 2022/0142904 | A1 | 5/2022 | Krohn et al. | |

FOREIGN PATENT DOCUMENTS

| DE | 102018213811 A1 | 2/2020 |
|---|---|---|
| DE | 102018218634 A1 | 4/2020 |
| DE | 102018132893 A1 | 6/2020 |
| DE | 102020207803 A1 | 12/2021 |
| DE | 102020208951 A1 | 1/2022 |
| EP | 2168633 B1 | 3/2016 |
| WO | 2020182476 A1 | 9/2020 |

OTHER PUBLICATIONS

Search Report dated May 19, 2022, of parallel PCT application No. PCT/EP2022/050857, 14 pages, for information purpose only.

* cited by examiner

*Primary Examiner* — Eisa B Elhilo
(74) *Attorney, Agent, or Firm* — Blank Rome LLP

(57) ABSTRACT

A method for dyeing keratinous material, in particular human hair, may include applying a first agent to the keratinous material. The first agent may include hydrogen peroxide. The method may further include applying a second agent to the keratinous material. The second agent may include at least one organosilicon compound from the group of silanes having one, two, or three silicon atoms. The method may further include applying a third agent to the keratinous material where the third agent includes at least one sealing reagent. At least one of the second or third agents may further include at least one dyeing compound from the group consisting of pigments and/or direct dyes.

20 Claims, No Drawings

METHOD FOR DYEING KERATINOUS MATERIAL, COMPRISING THE USE OF AN ORGANOSILICON COMPOUND, A DYEING COMPOUND, A SEALING REAGENT, AND A PRE-TREATMENT AGENT

CROSS-REFERENCE TO RELATED APPLICATIONS

The present application is a national stage entry according to 35 U.S.C. § 371 of PCT application No.: PCT/EP2022/050857 filed on Jan. 17, 2022; which claims priority to German patent application 10 2021 202 048.8 filed on Mar. 3, 2021; all of which are incorporated herein by reference in their entirety and for all purposes.

TECHNICAL FIELD

The subject of the present application is a method for treating keratinous material, in particular human hair, which comprises the application of two agents (a) and (b) and a pre-treatment agent. Agent (a) is characterized by its content of at least one organosilicon compound (a1). Agent (b) contains at least one sealing reagent (b1). Furthermore, either agent (a) or agent (b) contains or both agents (a) and (b) contain at least one dyeing compound from the group of pigments and/or the direct dyes. The pre-treatment agent comprises an oxidizing agent.

Another subject of this application is a multi-component packaging unit (kit-of-parts) for dyeing keratinous material, in particular human hair, which comprises at least three agents (a'), (a") and (b), packaged separately from one another, and one pre-treatment agent (v). The agent (a) used in the method described above can be prepared from agents (a') and (a").

Yet another subject of this application is a multi-component packaging unit (kit-of-parts) for dyeing keratinous material, in particular human hair, which comprises at least four agents (a'), (a"), (a''') and (b), packaged separately from one another, and one pre-treatment agent (v). The agent (a) used in the method described above can be prepared from agents (a'), (a") and (a''').

BACKGROUND

Changing the shape and color of keratinous fibers, in particular hair, represents an important area of modern cosmetics. To change the hair color, the skilled artisan is familiar with a variety of coloring system depending on the coloring requirements. Oxidation dyes are typically used for permanent, intense dyeing with good fastness properties and good gray coverage. Such coloring agents typically contain oxidation dye precursors, so-called developer components and coupler components, which together form the actual dyes under the influence of oxidizing agents, such as, for example, hydrogen peroxide. Oxidation dyes are characterized by very long-lasting color results.

When using direct dyes, dyes which are already formed diffuse out of the coloring agent into the hair fiber. In comparison with oxidative hair coloring, the colors obtained with direct dyes have a lower durability and a more rapid washing out. Colors with direct dyes usually remain on the hair for a period of between 5 and 20 hair washes.

The use of color pigments for brief changes in color on the hair and/or the skin is known. Color pigments are generally understood to mean insoluble dyeing substances. These are present undissolved in the form of small particles in the dyeing formulation and are only deposited from the outside onto the hair fibers and/or the skin surface. They can therefore generally be removed again without leaving residue by washing a few times with surfactant-containing cleaning agents. Various products of this type by the name of hair mascara are available on the market.

If the user desires particularly long-lasting colors, the use of oxidative coloring agents has hitherto been the only option. However, despite multiple optimization attempts, an unpleasant ammonia odor or amine odor cannot be completely avoided in oxidative hair dyeing. The hair damage that remains associated with the use of the oxidative coloring agents also has a disadvantageous effect on the hair of the user.

EP 2168633 B1 deals with the task of producing long-lasting hair coloring using pigments. The document teaches that, when using the combination of a pigment, an organosilicon compound, a film-forming polymer and a solvent on hair, colors can be produced which are particularly resistant to abrasion and/or shampooing.

There is a need to provide hair dyes with pigments which, on the one hand, do not adversely affect a high degree of wash- and friction-fastness and, on the other hand, hair properties such as handling and feel. For this purpose, it would be desirable to obtain intense dyes by a good and uniform coating of the pigments on the keratinous material.

Thus, the object of the present invention was to provide a dyeing system with pigments which has comparable fastness properties to oxidative dyeing. In particular, the wash-fastness properties should be outstanding, but the use of the oxidation dye precursors normally used for this purpose should be avoided. In particular, uniform and long-lasting coloration should also be achieved.

SUMMARY

Surprisingly, it has now been found that the aforementioned object can be successfully solved when keratinous materials, in particular human hair, are dyed using a method in which first a pre-treatment agent (v) containing hydrogen peroxide and then at least three agents (a) and (b) are applied to the keratinous materials (hair). In this case, the first agent (a) contains at least one organosilicon compound from the group of silanes having one, two or three silicon atoms. The second agent (b) contains at least one sealing reagent. Furthermore, either agent (a) or agent (b) contains or both agents (a) and (b) contain at least one dyeing compound from the group of pigments and/or the direct dyes.

When using the three agents (v), (a) and (b) in a dyeing method, it was possible to dye keratinous material with a particularly high color intensity and high fastness.

By pretreating the keratinous material with a pre-treatment agent containing hydrogen peroxide, a surprisingly uniform and long-lasting coating of the at least one dyeing compound was achieved.

DETAILED DESCRIPTION

A first subject of the present invention is a method for dyeing keratinous material, in particular human hair, comprising the following steps:
applying an agent (v) to the keratinous material, wherein agent (v) contains:
(v1) hydrogen peroxide,
applying an agent (a) to the keratinous material, wherein agent (a) contains:

(a1) at least one organosilicon compound from the group of silanes having one, two or three silicon atoms, and applying an agent (b) to the keratinous material, wherein agent (b) contains:
(b1) at least one sealing reagent,
wherein at least one of agents (a) and (b) additionally contains at least one dyeing compound from the group consisting of pigments and/or direct dyes.

In the work leading to this invention, it was found that the preferably successive application of agents (a) and (c) made it possible to produce highly stable and wash-fast colorings on the keratinous materials. The use of the organosilicon compound (a1) results in the formation of a particularly resistant film on the keratinous material. With the application of the second agent (b), the film applied on the keratinous material is sealed and thus rendered more resistant to washing and/or abrasion. By using at least one dyeing compound from the group of pigments and/or direct dyes in at least one of agents (a) and (b), colored films can be obtained.

In this way, the dyeing compounds can be durably fixed on the keratinous material such that it was possible to obtain extremely wash-fast colorings with good resistance to abrasion and/or shampooing.

With the aid of the pre-treatment agent, which comprises hydrogen peroxide, the adhesion and thus the durability of the films produced on the keratinous material could be significantly increased. It is assumed that the pre-treatment agent aligns the surface of the keratinous material and creates additional reactive sites on the surface of the keratinous material.

Keratinous Material

Keratin material is understood to mean hair, skin, and nails (such as, for example, fingernails and/or toenails). Furthermore, wool, furs and feathers also fall under the definition of the keratin material.

Keratin material is preferably understood to be human hair, human skin and human nails, in particular fingernails and toenails. Keratin material is very particularly preferably understood to mean human hair.

Pre-Treatment Agent (v)

Within the scope of the method described, a pre-treatment agent (v) is first applied to the keratinous material, in particular human hair. The pre-treatment agent (v) is characterized by a hydrogen peroxide (v1) content.

Hydrogen peroxide is an oxidizing agent which is usually used in the form of aqueous solutions. Accordingly, the pre-treatment agent (v) preferably also contains water in addition to hydrogen peroxide (v1).

The pre-treatment agent (v) contains the hydrogen peroxide in a preferred amount of 0.5 to 12 wt. %, more preferably of 1.9 to 12 wt. % and particularly preferably of 3 to 9 wt. %, the quantitative data being based on the total weight of pre-treatment agent (v).

According to a preferred embodiment of the method, the pre-treatment agent (v) comprises hydrogen peroxide (v1) in an amount of 0.5 to 12 wt. %, more preferably 1.9 to 12 wt. % and especially preferably 3 to 9 wt. %, in each case based on the total weight of the pre-treatment agent (v).

In addition to the hydrogen peroxide, the pre-treatment agent (v) can contain further ingredients, in particular surfactants or complexing agents.

In a preferred embodiment of the method, the pre-treatment agent (v) further comprises at least one surfactant.

The pre-treatment agent can further comprise anionic surfactants. According to a particularly preferred embodiment of the method, the pre-treatment agent (v) further comprises at least one anionic surfactant.

According to a preferred embodiment of the method, the anionic surfactants in the pre-treatment agent (v) are selected from the group consisting of:
straight-chain or branched, saturated or mono- or polyunsaturated alkyl sulfonates having 8 to 24, preferably 12 to 22, more preferably 16 to 18 C atoms,
linear alpha-olefin sulfonates having 8 to 24, preferably 12 to 22, more preferably 14 to 18 C atoms,
alkyl sulfates and alkyl polyglycol ether sulfates of the formula $R_9$—O—$(CH_2$—$CH_2O)_n$—$SO_3X$, where $R_9$ preferably represents a straight chain or branched, saturated or mono- or polyunsaturated alkyl or alkenyl radical having 8 to 24, preferably 12 to 22, more preferably 16 to 18 carbon atoms, n represents 0 or 1 to 12, more preferably 2 to 4 and X represents an alkali metal or alkaline earth metal ion or protonated triethanolamine or the ammonium ion,
straight chain or branched, saturated or mono- or polyunsaturated alkyl carboxylic acids having 8 to 24, preferably 12 to 22, more preferably 16 to 18 C atoms,
straight chain or branched, saturated or mono- or polyunsaturated alkyl phosphates having 8 to 24, preferably 12 to 22, more preferably 16 to 18 C atoms,
acyl isethionates whose acyl group is selected from a branched or unbranched $C_6$ to $C_{22}$, preferably $C_{10}$ to $C_{18}$, more preferably $C_{12}$ to $C_{16}$ alkyl group,
alkyl glycoside carboxylic acids whose alkyl group is selected from a branched or unbranched $C_6$ to $C_{22}$, preferably $C_{10}$ to $C_{18}$, more preferably $C_{12}$ to $C_{16}$ alkyl group,
alkyl sulfosuccinates whose two alkyl groups are selected from the same or different, branched or unbranched $C_2$ to $C_{12}$, preferably $C_4$ to $C_{10}$, more preferably $C_6$ to $C_8$ alkyl groups,
N-acyl taurates whose acyl group is selected from a branched or unbranched $C_6$ to $C_{22}$, preferably $C_8$ to $C_{18}$, more preferably $C_{12}$ to $C_{18}$ alkyl group,
alkyl sarcosinates whose alkyl group is selected from a branched or unbranched $C_6$ to $C_{22}$, preferably $C_{10}$ to $C_{18}$, more preferably $C_{12}$ to $C_{16}$ alkyl group,
sulfonates of unsaturated fatty acids having 8 to 24, preferably 12 to 22, more preferably 16 to 18 C atoms and 1 to 6 double bonds, and
mixtures thereof
wherein the counterion(s) of the anionic surfactant(s) comprises/comprise alkali or alkaline earth metal ions, protonated triethanolamine or the ammonium ion.

Particularly preferred anionic surfactants are straight chain or branched alkyl ether sulfates which contain an alkyl radical having 8 to 18 and in particular 10 to 16 C atoms and 1 to 6 and in particular 2 to 4 ethylene oxide units. Very particularly preferably, the at least one anionic surfactant comprises sodium lauryl ether sulfate (INCI: sodium laureth sulfate) and very particularly preferably sodium lauryl ether sulfate having two ethylene oxide units.

Further particularly preferred anionic surfactants are straight chain or branched alkyl sulfates which contain an alkyl radical having 8 to 18 and in particular 10 to 16 C atoms. The sodium, magnesium and/or triethanolamine salts of linear or branched lauryl, tridecyl, cetearyl and/or myristyl sulfates are particularly preferred. Very particular preference is given to the sodium salt of lauryl sulfate (INCI: sodium lauryl sulfate).

According to a preferred embodiment of the method, the pre-treatment agent (v) further contains at least one anionic surfactant comprising a sodium salt of lauryl sulfate.

Suitable surfactants also include in particular nonionic surfactants. According to a particularly preferred embodiment of the method, the pre-treatment agent (v) further comprises at least one nonionic surfactant.

According to a preferred embodiment of the method, the pre-treatment agent (v) further contains at least one nonionic surfactant selected from the group consisting of
alkyl glucamide comprising a saturated or unsaturated, branched or unbranched $C_6$ to $C_{22}$, preferably $C_{10}$ to $C_{18}$, more preferably $C_{12}$ to $C_{16}$ alkyl group,
alkyl(poly)glycoside comprising a saturated or unsaturated, branched or unbranched $C_6$ to $C_{22}$, preferably $C_{10}$ to $C_{18}$, more preferably $C_{12}$ to $C_{16}$ alkyl group,
alkyl alcohol alkoxylate of the formula $R_{10}(OR_{11})_m OH$, wherein $R_{10}$ is a linear or branched $C_6$ to $C_{22}$, preferably $C_{10}$ to $C_{18}$, more preferably $C_{12}$ to $C_{16}$ alkyl group, $R_{11}$ is a $C_2$ to $C_4$, preferably $C_2$ alkylene group, and m is from 1 to 10, preferably from 2 to 8, and
alkyl esters of the formula $R_{12}COOR_{13}$, wherein $R_{12}$ is a linear or branched $C_6$ to $C_{22}$, preferably $C_{10}$ to $C_{18}$, more preferably $C_{12}$ to $C_{16}$ alkyl group, $R_{13}$ is a Cu to $C_4$, preferably $C_2$ alkyl group.

Particularly preferred nonionic surfactants are alkyl(poly)glycosides of the general formula $RO—(Z)_x$, wherein R denotes an alkyl, Z denotes a sugar, and x denotes the number of sugar units. Those alkyl polyglycosides are particularly preferred in which R:
substantially consists of $C_8$ and $C_{10}$ alkyl groups or
substantially consists of $C_{12}$ and $C_{14}$ alkyl groups or
substantially consists of $C_8$ to $C_{18}$ alkyl groups or
substantially consists of $C_{12}$ to $C_{16}$ alkyl groups or
substantially consists of $C_{16}$ to $C_{18}$ alkyl groups Preferred alkyl(poly)glycosides contain on average 1.1 to 5 sugar units. Alkyl(poly)glycosides having x values of 1.1 to 2.0 are preferred. Alkylglycosides in which x is on average 1.1 to 1.8 are very particularly preferred.

Preferred sugar components are glucose, fructose, galactose, arabinose, and sucrose. It is very particularly preferred if Z is glucose. In this case, the alkyl(poly)glycoside is an alkyl(poly)glucoside.

A very particularly suitable alkyl(poly)glucoside is, for example, decyl glucoside which bears the CAS number 68515-73-1 and can be purchased commercially from BASF under the trade names Plantacare 2000 UP, Plantaren 2000 UP, and Plantaren 2000 UP N.

According to a preferred embodiment of the method, the pre-treatment agent (v) further contains at least one nonionic surfactant comprising an alkyl(poly)glucoside with the INCI name "decyl glucoside."

Other suitable nonionic surfactants include PEG derivatives of hydrogenated castor oil, which can be obtained, e.g., under the name PEG Hydrogenated Castor Oil, e.g., PEG-30 Hydrogenated Castor Oil, PEG-33 Hydrogenated Castor Oil, PEG-35 Hydrogenated Castor Oil, PEG-36 Hydrogenated Castor Oil, PEG-40 Hydrogenated Castor Oil or PEG-60 Hydrogenated Castor Oil.

Suitable surfactants also include, in particular, amphoteric surfactants. According to a particularly preferred embodiment of the method, the pre-treatment agent (v) further comprises at least one amphoteric surfactant.

Amphoteric surfactants, which are also known as zwitterionic surfactants, are surface-active compounds that bear at least one quaternary ammonium group and at least one $—COO^-$ or $—SO_3^-$ group in the molecule. "Amphoteric/zwitterionic surfactants" also refers to those surface-active compounds that contain at least one free amino group and at least one $—COOH—$ or $—SO_3H—$ group in addition to a $C_8$-$C_{24}$ alkyl or acyl group, and are capable of forming zwitterions.

According to a preferred embodiment of the method, the pre-treatment agent (v) further contains at least one amphoteric surfactant selected from the group consisting of
alkyl betaine comprising at least one saturated or unsaturated, branched or unbranched $C_6$ to $C_{22}$, preferably $C_{10}$ to $C_{18}$, more preferably $C_{12}$ to $C_{16}$ alkyl group,
alkyl amphodiacetate or alkyl amphodiacetate comprising a saturated or unsaturated, branched or unbranched $C_6$ to $C_{22}$, preferably $C_{10}$ to $C_{18}$, more preferably $C_{12}$ to $C_{16}$ alkyl group, with an alkali metal or alkaline earth metal counterion, and
alkylamidopropyl betaine comprising at least one saturated or unsaturated, branched or unbranched $C_6$ to $C_{22}$, preferably $C_{10}$ to $C_{18}$, more preferably $C_{12}$ to $C_{16}$ alkyl group.

The particularly suitable amphoteric/zwitterionic surfactants include the surfactants known under the INCI name "cocamidopropyl betaine," "disodium cocoamphodiacetate" and "cocoyl dimethyl betaine."

The agent (c) contains the at least one hydroxyamine-functionalized silicone polymer in a preferred amount of 1 to 20 wt. %, more preferably of 2.5 to 17.5 and particularly preferably of 5 to 15 wt. %, the quantitative data being based on the total weight of agent (c).

It is believed that the surfactants help to align the surface of the keratinous material and, for example, remove existing product residues (for example, residues of styling products applied) and/or substantive compounds (for example, conditioning polymers of conditioners applied) that prevent a uniform and long-lasting lifting of the film formed by the application of the organosilicon compound (a1).

According to a preferred embodiment of the method, the pre-treatment agent (v) contains from 3 to 9 wt. % of hydrogen peroxide and further from 5 to 15 wt. % of alkyl(poly)glucoside, in each case based on the total weight of the pre-treatment agent (v).

In this embodiment, it is preferable for the pH of the pre-treatment agent (v) to be in the acidic pH range, in particular in the range of 4 to 5.

According to a preferred embodiment of the method, the pre-treatment agent (v) further contains at least one complexing agent.

According to a more preferred embodiment of the method, the pre-treatment agent (v) further contains at least one complexing agent selected from the group consisting of complexing agents selected from the group consisting of
nitrotriacetic (NTA),
diethylenetriaminepentaacetic acid (DPTA),
ethylenediaminedisuccinic acid (EDDS),
ethylenediaminediglutaric acid (EDGA),
2-hydroxypropylenediaminedisuccinic acid (HPDS),
(f) glycinamide-N—N'-disuccinic acid (GADS),
(g) ethylenediamine-N—N'-diglutaric acid (EDDG),
(h) 2-hydroxypropylenediamine-N—N'-disuccinic acid (HPDDS),
(i) ethylenediaminetetraacetic acid (EDTA),
(j) ethylenedicysteic acid (EDC),
(k) diaminoalkyldi(sulfosuccinic acid) (DDS),
(l) ethylenediamine-N—N'-bis(ortho-hydroxyphenylacetic acid (EDDHA),
(m) N-2-hydroxyethyl-N,N-diacetic acid,
(n) glyceryliminodiacetic acid, (o) iminodiacetic acid-N-2-hydroxypropylsulfonic acid,
(p) aspartic acid-N-carboxymethyl-N-2,5-hydroxypropyl-3-sulfonic acid,
(q) α-alanine-N,N'-diacetic acid,
(r) aspartic acid-N,N'-diacetic acid,
(s) aspartic acid-N-monoacetic acid,
(t) dipicolinic acid,
(u) 1-hydroxyethane-(1,1-diphosphonic acid) (HEDP), and
(v) salts and derivatives thereof.

According to a preferred embodiment of the method, the pre-treatment agent (v) contains 3 to 9 wt. % of hydrogen peroxide and further comprises a complexing agent comprising 1-hydroxyethane-(1,1-diphosphonic acid) (HEDP).

According to a preferred embodiment of the method, the pre-treatment agent (v) contains, based on its weight, the at least one complexing agent in a total amount of from 0.01 to 12 wt. %, more preferably from 0.1 to 6 wt. % and most preferably from 0.2 to 3 wt. %.

It may be preferable for the pH of the agent (v) to be alkaline. In this embodiment, the pre-treatment agent further contains an alkalizing agent.

Suitable alkalizing agents include, for example, hydroxides, such as sodium hydroxide; carbonates, such as magnesium carbonate; alkanolamines, such as monoethanolamine; and/or basic amino acids.

In this embodiment, it is preferable for the pH of the pre-treatment agent (v) to be in the range of 9 to 10.

Agents (a) and (b)

In the context of the described method, agents (a) and (b) are applied to the keratinous material, in particular human hair, after the pre-treatment agent (v). The two agents (a) and (b) are different to each other.

Agent (a)

The agent (a) preferably contains the ingredient (a1) essential to the invention in a cosmetic carrier, particularly preferably in an aqueous or aqueous-alcoholic cosmetic carrier. This cosmetic carrier can be in the form of a liquid, gel or cream. Pasty, solid or pulverulent cosmetic carriers can also be used to produce the agent (a). For the purpose of hair treatment, in particular hair dyeing, such carriers are for example creams, emulsions, gels or else surfactant-containing foaming solutions, for example shampoos, foam aerosols, form formulations or other preparations which are suitable for application to hair.

Preferably, the cosmetic carrier contains, relative to the weight thereof, at least 2 wt % water. More preferably, the water content is greater than 10 wt %, even more preferably greater than 20 wt % and particularly preferably greater than 40 wt %. The cosmetic carrier can also be aqueous-alcoholic. Within the meaning of the present invention, aqueous-alcoholic solutions are aqueous solutions containing 2 to 70 wt % of a $C_1$-$C_4$ alcohol, in particular ethanol or isopropanol. The agents can additionally contain further organic solvents, such as for example methoxybutanol, benzyl alcohol, ethyl diglycol or 1,2-propylene glycol. Thus all water-soluble organic solvents are preferred.

Organosilicon Compounds from the Group of Silanes (A1)

As ingredient (a1) essential to the invention, agent (a) contains at least one organosilicon compound from the group of silanes having one, two or three silicon atoms.

Particularly, preferably, agent (a) contains at least one organosilicon compound (a1) selected from silanes having one, two or three silicon atoms, wherein the organosilicon compound comprises one or more hydroxyl groups and/or hydrolyzable groups per molecule.

The organosilicon compounds (a1) or organosilanes in the agent (a) are reactive compounds.

Organosilicon compounds, which are alternatively also referred to as organic silicon compounds, are compounds which either have a direct silicon-carbon bond (Si—C), or in which the carbon is linked to the silicon atom via an oxygen, nitrogen or sulfur atom. The organosilicon compounds according to the invention are compounds which contain one to three silicon atoms. The organosilicon compounds particularly preferably contain one or two silicon atoms.

According to the IUPAC rules, the term silane represents a substance group of chemical compounds based on a silicon backbone and hydrogen. In the case of organosilanes, the hydrogen atoms are completely or partially replaced by organic groups such as (substituted) alkyl groups and/or alkoxy groups. Some of the hydrogen atoms can also be replaced by hydroxyl groups in the organosilanes.

In the context of a particularly preferred embodiment, a method is characterized by the application of an agent (a) to the keratinous material, wherein the agent (a) contains at least one organosilicon compound (a1) selected from silanes having one, two or three silicon atoms, wherein the organosilicon compound also comprises one or more hydroxyl groups or hydrolyzable groups per molecule.

In the context of a very particularly preferred embodiment, a method is characterized by the application of an agent (a) to the keratinous material, wherein the agent (a) contains at least one organosilicon compound (a1) selected from silanes having one, two or three silicon atoms, wherein the organosilicon compound also comprises one or more basic chemical functions and one or more hydroxyl groups or hydrolyzable groups per molecule.

This basic group or basic chemical function may be, for example, an amino group, an alkylamino group, a dialkylamino group or a trialkylamino group which is preferably connected to a silicon atom via a linker. Preferably, the basic group is an amino group, a $C_1$-$C_6$ alkylamino group or a di($C_1$-$C_6$) alkylamino group.

The hydrolyzable group(s) are preferably a $C_1$-$C_6$ alkoxy group, in particular an ethoxy group or a methoxy group. It is preferred if the hydrolyzable group is present directly bound to the silicon atom. If, for example, the hydrolyzable group is an ethoxy group, the organosilicon compound preferably contains a structural unit R'R''R'''Si—O—CH$_2$—CH$_3$. The R'R''R''' functional groups here represent the three remaining free valencies of the silicon atom.

A very particularly preferred method is characterized in that agent (a) contains at least one organosilicon compound selected from silanes having one, two or three silicon atoms, wherein the organosilicon compound preferably comprises one or more basic chemical functions and one or more hydroxyl groups or hydrolyzable groups per molecule.

Excellent results were obtained when the agent (a) contained at least one organosilicon compound (a1) of formula (I) and/or (II).

The compounds of formulas (I) and (II) are organosilicon compounds selected from silanes with one, two or three silicon atoms, wherein the organosilicon compound comprises one or more hydroxyl groups and/or hydrolyzable groups per molecule.

In a further very particularly preferred embodiment, the method is characterized in that an agent is applied to the keratinous material (or the human hair), wherein agent (a) contains at least one organosilicon compound (a) of formula (I) and/or (II), $$R_1R_2N\text{-}L\text{-}Si(OR_3)_a(R_4)_b \qquad (I),$$

wherein
R$_1$ and R$_2$ represent, independently of one another, a hydrogen atom or a C$_1$-C$_6$ alkyl group,
L represents a linear or branched divalent C$_1$-C$_{20}$ alkylene group,
R$_3$ represents a hydrogen atom or a C$_1$-C$_6$ alkyl group,
R$_4$ represents a C$_1$-C$_6$ alkyl group
a represents an integer from 1 to 3, and
b represents the integer 3−a, $$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{-}Si(R_{6'})_{d'}(OR_{5'})_{c'} \quad (II),$$

wherein
R$_5$, R$_{5'}$, R$_{5''}$ represent, independently of one another, a hydrogen atom or a C$_1$-C$_6$ alkyl group,
R$_6$, R$_{6'}$ and R$_{6''}$ represent, independently of one another, a C$_1$-C$_6$ alkyl group,
A, A', A'', A''' and A'''' represent, independently of one another, a linear or branched, divalent C$_1$-C$_{20}$ alkylene group,
R$_7$ and R$_8$ represent, independently of one another, a hydrogen atom, a C$_1$-C$_6$ alkyl group, a hydroxy C$_1$-C$_6$ alkyl group, a C$_2$-C$_6$ alkenyl group, an amino C$_1$-C$_6$ alkyl group or a group of formula (III), $$(A'''')\text{-}Si(R_{6''})_{d''}(R_{5''})_{c''} \quad (III),$$

c represents an integer from 1 to 3,
d represents the integer 3−c,
c' represents an integer from 1 to 3,
d' represents the integer 3−c',
c'' represents an integer from 1 to 3,
d'' represents the integer 3−c',
e represents 0 or 1,
f represents 0 or 1,
g represents 0 or 1, and
h represents 0 or 1,
with the proviso that at least one of the functional groups e, f, g and h is different from 0.

The substituents R$_1$, R$_2$, R$_3$, R$_4$, R$_5$, R$_{5'}$, R$_{5''}$, R$_6$, R$_{6'}$, R$_{6''}$, R$_7$, R$_8$, L, A, A', A'', A''' and A'''' in the compounds of formula (I) and (II) are explained by way of example below:

Examples of a C$_1$-C$_6$ alkyl group are the groups methyl, ethyl, propyl, isopropyl, n-butyl, s-butyl and t-butyl, n-pentyl and n-hexyl. Propyl, ethyl and methyl are preferred alkyl functional groups. Examples of a C$_2$-C$_6$ alkenyl group are vinyl, allyl, but-2-enyl, but-3-enyl and isobutenyl; preferred C$_2$-C$_6$alkenyl functional groups are vinyl and allyl. Preferred examples of a hydroxy-C$_1$-C$_6$ alkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is particularly preferred. Examples of an amino-C$_1$-C$_6$ alkyl group are the aminomethyl group, the 2-aminoethyl group, and the 3-aminopropyl group. The 2-aminoethyl group is particularly preferred. Examples of a linear divalent C$_1$-C$_{20}$ alkylene group are, for example, the methylene group (—CH$_2$—), the ethylene group (—CH$_2$—CH$_2$—), the propylene group (—CH$_2$—CH$_2$—CH$_2$—) and the butylene group (CH$_2$—CH$_2$—CH$_2$—CH$_2$—). The propylene group (—CH$_2$—CH$_2$—CH$_2$—) is particularly preferred. Starting at a chain length of 3 C atoms, divalent alkylene groups may also be branched. Examples of branched, divalent C$_3$-C$_{20}$ alkylene groups are (—CH$_2$—CH(CH$_3$)—) and (—CH$_2$—CH(CH$_3$)—CH$_2$—).

In the organosilicon compound of formula (I)

$$R_1R_2N\text{-}L\text{-}Si(OR_3)_a(R_4)_b \quad (I),$$

the functional groups R$_1$ and R$_2$ represent, independently of one another, a hydrogen atom or a C$_1$-C$_6$ alkyl group. Most preferably, the functional groups R$_1$ and R$_2$ both represent a hydrogen atom.

In the middle part of the organosilicon compound, the structural unit or linker -L- is located, which represents a linear or branched divalent C$_1$-C$_{20}$ alkylene group.

A divalent C$_1$-C$_{20}$ alkylene group can alternatively also be referred to as a divalent or doubly-bonding C$_1$-C$_{20}$ alkylene group, with this meaning that each group L can participate in two bonds. One bond is from the amino group R$_1$R$_2$N to the linker L, and the second bond is between the linker L and the silicon atom.

Preferably, -L- represents a linear divalent C$_1$-C$_{20}$ alkylene group. More preferably, -L- represents a linear divalent C$_1$-C$_6$ alkylene group. Particularly preferably, -L- represents a methylene group (—CH$_2$—), an ethylene group (—CH$_2$—CH$_2$—), a propylene group (—CH$_2$—CH$_2$—CH$_2$—) or a butylene group (—CH$_2$—CH$_2$—CH$_2$—CH$_2$—). Most preferably, L represents a propylene group (—CH$_2$—CH$_2$—CH$_2$—).

The linear propylene group (—CH$_2$—CH$_2$—CH$_2$—) can alternatively also be referred to as a propane-1,3-diylgroup.

The organosilicon compounds of formula (I)

$$R_1R_2N\text{-}L\text{-}Si(OR_3)_a(R_4)_b \quad (I),$$

each bear, on one end, the silicon-containing group —Si(OR$_3$)$_a$(R$_4$)$_b$.

In the terminal structural unit —Si(OR$_3$)$_a$(R$_4$)$_b$, the functional group R$_3$ represents a hydrogen atom or a C$_1$-C$_6$ alkyl group, and the functional group R$_4$ represents a C$_1$-C$_6$ alkyl group. Particularly preferably, R$_3$ and R$_4$ represent, independently of one another, a methyl group or an ethyl group.

In this case, a represents an integer from 1 to 3, and b represents the integer 3-a. If a represents the number 3, then b is equal to 0. If a represents the number 2, then b is equal to 1. If a represents the number 1, then b is equal to 2.

Particularly resistant films were obtained when agent (a) contained at least one organosilicon compound (a1) of formula (I), in which the functional groups R$_3$ and R$_4$ represent, independently of one another, a methyl group or an ethyl group.

When using the method for dyeing keratinous material, it was thus analogously possible to obtain colorings with the best wash fastness when agent (a) contained at least one organosilicon compound of formula (I), in which the functional groups R$_3$ and R$_4$ represent, independently of one another, a methyl group or an ethyl group.

Furthermore, it was possible to obtain colorings with the best wash-fastness when agent (a) contained at least one organosilicon compound of formula (l) in which the functional group a represents the number 3. In this case, the functional group b represents the number 0.

In another preferred embodiment, the agent (a) used in the method is characterized in that it contains at least one organosilicon compound (a1) of formula (I), wherein
R$_3$ and R$_4$ represent, independently of one another, a methyl group or an ethyl group, and
a represents the number 3, and
b represents the number 0.

In another preferred embodiment, a method is characterized in that agent (a) contains at least one organosilicon compound (a1) of formula (I), $$R_1R_2N\text{-}L\text{-}Si(OR_3)_a(R_4)_b \quad (I),$$

wherein
- $R_1$ and $R_2$ both represent a hydrogen atom, and
- L represents a linear, divalent $C_1$-$C_6$ alkylene group, preferably a propylene group (—$CH_2$—$CH_2$—$CH_2$—) or an ethylene group (—$CH_2$—$CH_2$—),
- $R_3$ represents a hydrogen atom, an ethyl group or a methyl group,
- $R_4$ represents a methyl group or an ethyl group,
- a represents the number 3, and
- b represents the number 0.

To achieve the object according to the invention, particularly well-suited organosilicon compounds of formula (I) are

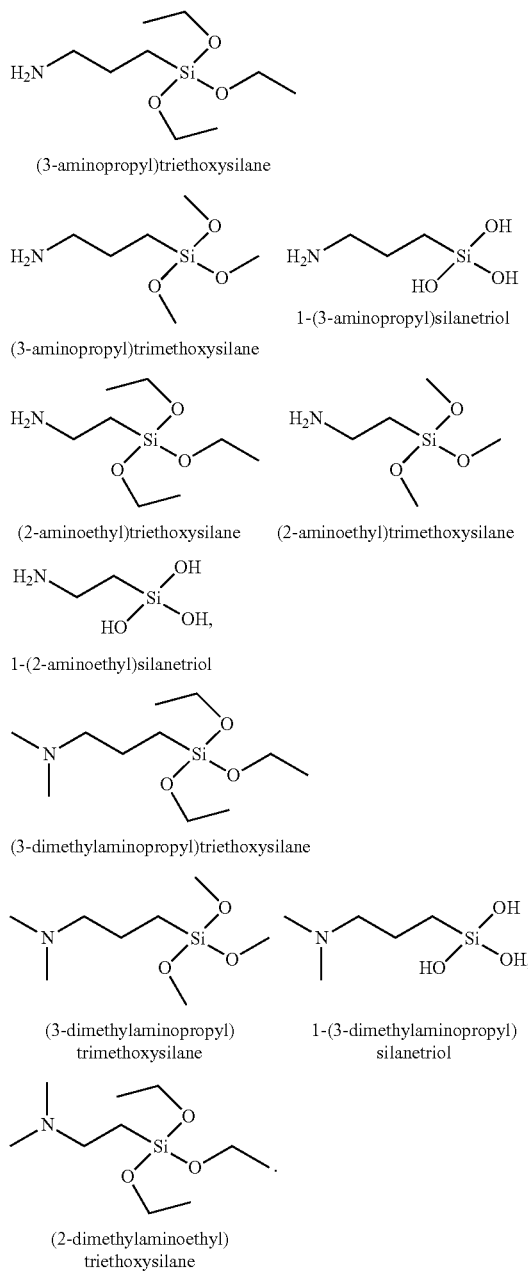

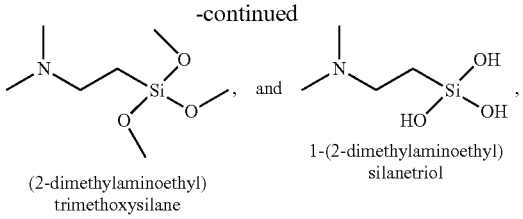

(2-dimethylaminoethyl) trimethoxysilane, and 1-(2-dimethylaminoethyl) silanetriol In another preferred embodiment, a method is characterized in that agent (a) contains at least one organosilicon compound (a1) selected from the group of
- (3-aminopropyl)triethoxysilane
- (3-aminopropyl)trimethoxysilane
- 1-(3-aminopropyl)silanetriol
- (2-aminoethyl)triethoxysilane
- (2-aminoethyl)trimethoxysilane
- 1-(2-aminoethyl)silanetriol,
- (3-dimethylaminopropyl)triethoxysilane
- (3-dimethylaminopropyl)trimethoxysilane
- 1-(3-dimethylaminopropyl)silanetriol,
- (2-dimethylaminoethyl)triethoxysilane.
- (2-dimethylaminoethyl)trimethoxysilane, and/or
- 1-(2-dimethylaminoethyl)silanetriol.

The aforementioned organosilicon compounds of formula (I) are commercially available.

(3-aminopropyl)trimethoxysilane can be purchased from Sigma-Aldrich, for example. (3-aminopropyl)triethoxysilane is commercially available from Sigma-Aldrich.

In the context of another embodiment, the agent contains at least one organosilicon compound (a1) of formula (II)

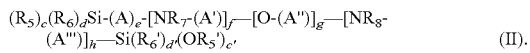

The organosilicon compounds of formula (II) each bear the silicon-containing groups $(R_5O)_c(R_6)_dSi$— and —$Si(R_6')_{d'}(OR_5')_{c'}$ at their two ends.

The groups -(A)$_e$- and —[$NR_7$-(A')]$_f$- are in the middle part of the molecule of formula (II) and —[O-(A'')]$_g$- and —[$NR_8$-(A''')]$_h$-. In this case, each of the functional groups e, f, g and h can independently represent the number 0 or 1, with the proviso that at least one of the functional groups e, f, g and h is different from 0. In other words, an organosilicon compound of formula (II) contains at least one grouping from the group consisting of -(A)- and —[$NR_7$-(A')]- and —[O-(A'')]- and —[$NR_8$-(A''')]-.

In the two terminal structural units $(R_5O)_c(R_6)_dSi$— and —$Si(R_6')_{d'}(OR_5')_{c'}$, the functional groups $R_5$, $R_5'$ and $R_{5''}$ represent, independently of one another, a hydrogen atom or a $C_1$-$C_6$ alkyl group. The functional groups $R_6$, $R_{6'}$ and $R_{6''}$ represent, independently of one another, a $C_1$-$C_6$ alkyl group.

In this case, c is an integer from 1 to 3, and d is the integer 3−c. If c represents the number 3, then d is equal to 0. If c represents the number 2, then d is equal to 1. If c represents the number 1, then d is equal to 2.

Similarly, c' represents an integer of 1 to 3, and d' represents the integer 3−c'. If c' represents the number 3, then d' is equal to 0. If c' represents the number 2, then d' is equal to 1. If c' represents the number 1, then d' is equal to 2.

It was possible to obtain films with the highest stability, or colorings with the best wash-fastness, when the functional groups c and c' both represented the number 3. In this case, d and d' both represent the number 0.

In another preferred embodiment, a method is characterized in that agent (a) contains at least one organosilicon compound (a1) of formula (II),

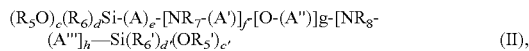 (II), wherein $R_5$ and $R_5'$ represent, independently of each other, a methyl group or an ethyl group, c and c' both represent the number 3, and d and d' both represent the number 0.

If c and c' both represent the number 3 and d and d' both represent the number 0, the inventive organosilicon compound of formula (IIa) corresponds to:

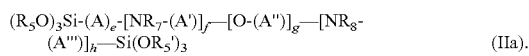 (IIa).

The functional groups e, f, g and h can independently represent the number 0 or 1, where at least one functional group of e, f, g and h is different from zero. The abbreviations e, f, g and h therefore define which of the groupings $-(A)_e-$, $-[NR_7-(A')]_f-$, $-[O-(A'')]_g-$ and $-[NR_8-(A''')]_h-$ are located in the middle part of the organosilicon compound of formula (II).

In this context, the presence of certain groupings has proven to be particularly advantageous with regard to increasing wash fastness. Particularly good results were obtained when at least two of the functional groups e, f, g and h represented the number 1. Most preferably, e and f both represent the number 1. Furthermore, g and h very particularly preferably both represent the number 0.

If e and f both represent the number 1, and g and h both represent the number 0, the organosilicon compound according to the invention corresponds to formula (IIb):

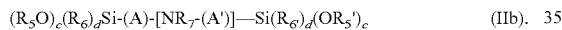 (IIb).

The functional groups A, A', A'', A''' and A'''' represent, independently of one another, a linear or branched divalent $C_1$-$C_{20}$ alkylene group. A, A', A'', A''' and A'''' preferably represent, independently of one another, a linear or branched divalent $C_1$-$C_{20}$ alkylene group. More preferably, the functional groups A, A', A'', A''' and A'''' represent, independently of one another, a linear divalent $C_1$-$C_6$ alkylene group. Particularly preferably, the functional groups A, A', A'', A''' and A'''' represent, independently of one another, a methylene group (—$CH_2$—), an ethylene group (—$CH_2$—$CH_2$—), a propylene group (—$CH_2$—$CH_2$—$CH_2$—) or a butylene group (—$CH_2$—$CH_2$—$CH_2$—$CH_2$—). Very particularly preferably, the functional groups A, A', A'', A''' and A'''' represent a propylene group (—$CH_2$—$CH_2$—$CH_2$—).

The divalent $C_1$-$C_{20}$ alkylene group can alternatively also be referred to as a divalent or doubly-bonding $C_1$-$C_{20}$ alkylene group, with this meaning that each group A, A', A'', A''' and A'''' can participate in two bonds.

The linear propylene group (—$CH_2$—$CH_2$—$CH_2$—) can alternatively also be referred to as a propane-1,3-diyl group.

If the functional group f represents the number 1, the organosilicon compound of formula (II) contains a structural group —[$NR_7$-(A')]-.

If the functional group h represents the number 1, the organosilicon compound of formula (II) contains a structural group —[$NR_8$-(A''')]-.

In this context, $R_7$ and $R_8$ represent, independently of one another, a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (III):

 (III).

Most preferably, the functional groups R7 and R8 represent, independently of one another, a hydrogen atom, a methyl group, a 2-hydroxyethyl group, a 2-alkenyl group, a 2-aminoethyl group or a grouping of formula (III).

If the group f represents the number 1 and the group h represents the number 0, the organosilicon compound contains the grouping [$NR_7$-(A')], but not the grouping —[$NR_8$-(A''')]. If the functional group R7 then represents a group of formula (III), agent (a) contains an organosilicon compound having 3 reactive silane groups.

In another preferred embodiment, a method is characterized in that agent (a) contains at least one organosilicon compound (a1) of formula (II),

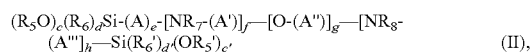 (II), wherein e and f both represent the number 1, g and h both represent the number 0, A and A' represent, independently of one another, a linear, divalent $C_1$-$C_6$ alkylene group, and $R_7$ represents a hydrogen atom, a methyl group, a 2-hydroxyethyl group, a 2-alkenyl group, a 2-aminoethyl group or a group of formula (III).

In another preferred embodiment, a method is characterized in that agent (a) contains at least one organosilicon compound of formula (II), wherein e and f both represent the number 1, g and h both represent the number 0, A and A' represent, independently of one another, a methylene group (—$CH_2$—), an ethylene group (—$CH_2$—$CH_2$—) or a propylene group (—$CH_2$—$CH_2$—$CH_2$—), and $R_7$ represents a hydrogen atom, a methyl group, a 2-hydroxyethyl group, a 2-alkenyl group, a 2-aminoethyl group or a group of formula (III).

To achieve the object according to the invention, well-suited organosilicon compounds of formula (II) are

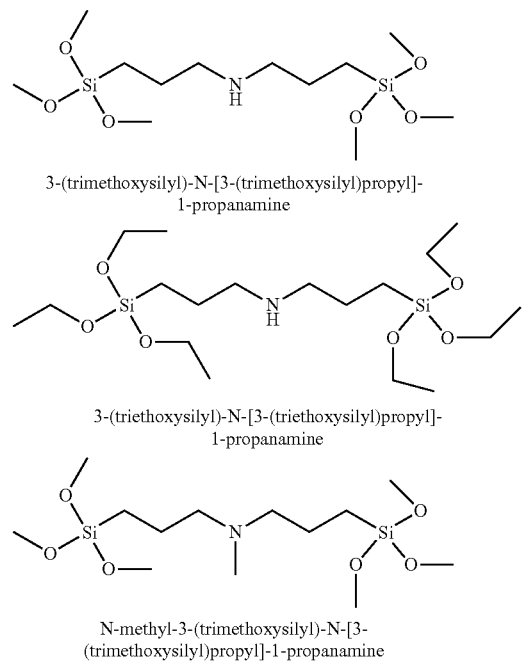

3-(trimethoxysilyl)-N-[3-(trimethoxysilyl)propyl]-1-propanamine 3-(triethoxysilyl)-N-[3-(triethoxysilyl)propyl]-1-propanamine N-methyl-3-(trimethoxysilyl)-N-[3-(trimethoxysilyl)propyl]-1-propanamine

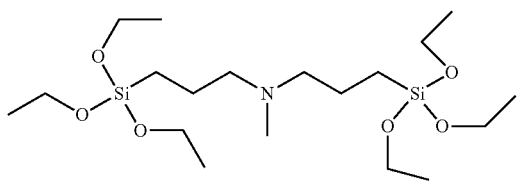

N-methyl-3-(triethoxysilyl)-N-[3-(triethoxysilyl)propyl]-1-propanamine

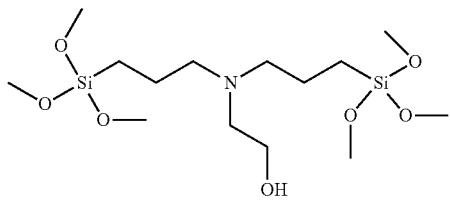

2-[bis[3-(trimethoxysilyl)propyl]amino]ethanol

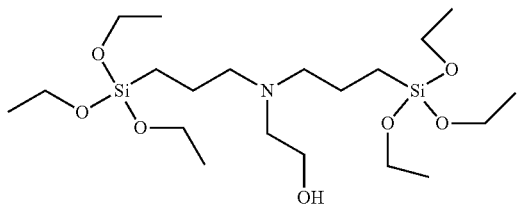

2-[bis[3-(triethoxysilyl)propyl]amino]ethanol

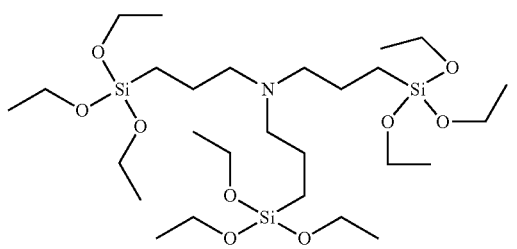

3-(triethoxysilyl)-N,N-bis[3-(triethoxysilyl)propyl]-1-propanamine

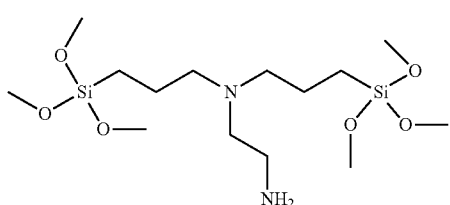

N1,N1-bis[3-(trimethoxysilyl)propyl]-1,2-ethanediamine

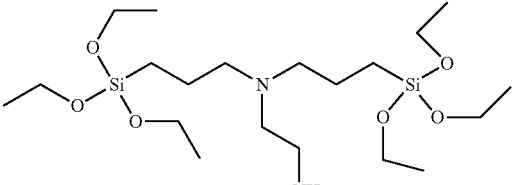

N1,N1-bis[3-(triethoxysilyl)propyl]-1,2-ethanediamine

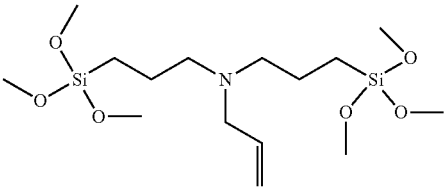

N,N-bis[3-(trimethoxysilyl)propyl]-2-propen-1-amine

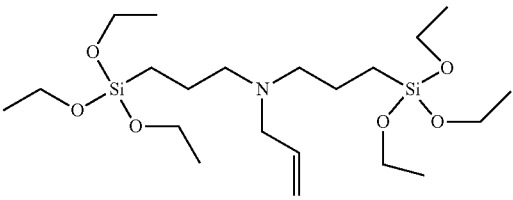

N,N-bis[3-(triethoxysilyl)propyl]-2-propen-1-amine

The aforementioned organosilicon compounds of formula (II) are commercially available.

Bis(trimethoxysilylpropyl)amine with the CAS number 82985-35-1 can, for example, be purchased from Sigma-Aldrich.

Bis[3-(triethoxysilyl)propyl]amines with the CAS number 13497-18-2 can be purchased from Sigma-Aldrich, for example.

N-methyl-3-(trimethoxysilyl)-N-[3-(trimethoxysilyl)propyl]-1-propanamine is alternatively also referred to as bis (3-trimethoxysilylpropyl)-N-methylamine and can be purchased commercially from Sigma-Aldrich or Fluorochem.

3-(triethoxysilyl)-N,N-bis[3-(triethoxysilyl)propyl]-1-propanamine with the CAS number 18784-74-2 can be purchased, for example, from Fluorochem or Sigma-Aldrich.

In another preferred embodiment, a method is characterized in that agent (a) contains at least one organosilicon compound (a1) selected from the group of
  3-(trimethoxysilyl)-N-[3-(trimethoxysilyl)propyl]-1-propanamine
  3-(triethoxysilyl)-N-[3-(triethoxysilyl)propyl]-1-propanamine
  N-methyl-3-(trimethoxysilyl)-N-[3-(trimethoxysilyl)propyl]-1-propanamine
  N-methyl-3-(triethoxysilyl)-N-[3-(triethoxysilyl)propyl]-1-propanamine
  2-[bis[3-(trimethoxysilyl)propyl]amino]ethanol
  2-[bis[3-(triethoxysilyl)propyl]amino]ethanol
  3-(trimethoxysilyl)-N,N-bis[3-(trimethoxysilyl)propyl]-1-propanamine
  3-(triethoxysilyl)-N,N-bis[3-(triethoxysilyl)propyl]-1-propanamine
  N1,N1-bis[3-(trimethoxysilyl)propyl]-1,2-ethanediamine
  N1,N1-bis[3-(triethoxysilyl)propyl]-1,2-ethanediamine
  N,N-bis[3-(trimethoxysilyl)propyl]-2-propen-1-amine, and/or
  N,N-bis[3-(triethoxysilyl)propyl]-2-propen-1-amine.

In further experiments, in particular dyeing experiments, it has also been found to be very particularly advantageous if agent (a) applied, in the method, to the keratinous material contains at least one organosilicon compound of formula (IV)

The compounds of formula (IV) are organosilicon compounds selected from silanes with one, two or three silicon atoms, wherein the organosilicon compound comprises one or more hydroxyl groups and/or hydrolyzable groups per molecule.

The organosilicon compound(s) of formula (IV) can also be referred to as silanes of the alkyl alkoxysilanes type or alkyl hydroxysilanes, $R_9Si(OR_{10})_k(R_{11})_m$ (IV), wherein
$R_9$ represents a $C_1$-$C_{18}$ alkyl group,
$R_{10}$ represents a hydrogen atom or a $C_1$-$C_6$ alkyl group,
$R_{11}$ represents a $C_1$-$C_6$ alkyl group
k represents an integer from 1 to 3, and
m represents the integer 3−k.

In another preferred embodiment, the method is characterized in that agent (a) contains at least one organosilicon compound (a1) of formula (IV)

$R_9Si(OR_{10})_k(R_{11})_m$ (IV), wherein
$R_9$ represents a $C_1$-$C_{18}$ alkyl group,
$R_{10}$ represents a hydrogen atom or a $C_1$-$C_6$ alkyl group,
$R_{11}$ represents a $C_1$-$C_6$ alkyl group
k represents an integer from 1 to 3, and
m represents the integer 3−k.

In another preferred embodiment, a method is characterized in that, in addition to the organosilicon compound(s) of formula (I), agent (a) contains at least one further organosilicon compound of formula (IV)

$R_9Si(OR_{10})_k(R_{11})_m$ (IV), wherein
$R_9$ represents a $C_1$-$C_{18}$ alkyl group,
$R_{10}$ represents a hydrogen atom or a $C_1$-$C_6$ alkyl group,
$R_{11}$ represents a $C_1$-$C_6$ alkyl group
k represents an integer from 1 to 3, and
m represents the integer 3−k.

In another preferred embodiment, a method is characterized in that, in addition to the organosilicon compound(s) of formula (II), agent (a) contains at least one further organosilicon compound of formula (IV)

$R_9Si(OR_{10})_k(R_{11})_m$ (IV), wherein
$R_9$ represents a $C_1$-$C_{18}$ alkyl group,
$R_{10}$ represents a hydrogen atom or a $C_1$-$C_6$ alkyl group,
$R_{11}$ represents a $C_1$-$C_6$ alkyl group
k represents an integer from 1 to 3, and
m represents the integer 3−k.

In another preferred embodiment, a method is characterized in that, in addition to the organosilicon compound(s) of formula (I) and/or (II), agent (a) contains at least one further organosilicon compound of formula (IV)

$R_9Si(OR_{10})_k(R_{11})_m$ (IV), wherein
$R_9$ represents a $C_1$-$C_{18}$ alkyl group,
$R_{10}$ represents a hydrogen atom or a $C_1$-$C_6$ alkyl group,
$R_{11}$ represents a $C_1$-$C_6$ alkyl group
k represents an integer from 1 to 3, and
m represents the integer 3−k.

In the organosilicon compounds of formula (IV), the functional group $R_9$ represents a $C_1$-$C_{18}$ alkyl group. This $C_1$-$C_{18}$ alkyl group is saturated and can be linear or branched. $R_9$ preferably represents a linear $C_1$-$C_{18}$ alkyl group. Preferably, $R_9$ represents a methyl group, an ethyl group, an n-propyl group, an n-butyl group, an n-pentyl group, an n-hexyl group, an n-octyl group, an n-dodecyl group or an n-octyldecyl group. Particularly preferably, $R_9$ represents a methyl group, an ethyl group, an n-hexyl group or an n-octyl group.

In the organosilicon compounds of formula (IV), the functional group $R_{10}$ represents a hydrogen atom or a $C_1$-$C_6$ alkyl group. Particularly preferably, $R_{10}$ represents a methyl group or an ethyl group.

In the organosilicon compounds of formula (IV), the functional group $R_{11}$ represents a $C_1$-$C_6$ alkyl group. Particularly preferably, $R_{11}$ represents a methyl group or an ethyl group.

Furthermore, k represents an integer from 1 to 3, and m represents the integer 3−k. If k represents the number 3, then m is equal to 0. If k represents the number 2, then m is equal to 1. If k represents the number 1, then m is equal to 2.

It was possible to obtain particularly stable films, i.e. colorings with particularly good wash-fastness, when an agent (a), containing at least one organosilicon compound (a1) of formula (IV) in which the functional group k represents the number 3, was used in the method. In this case, the functional group m represents the number 0.

To achieve the object according to the invention, particularly well-suited organosilicon compounds of formula (IV) are

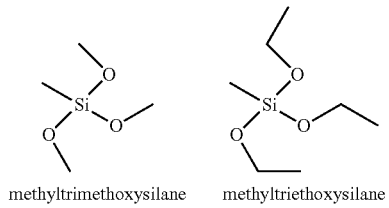

methyltrimethoxysilane    methyltriethoxysilane

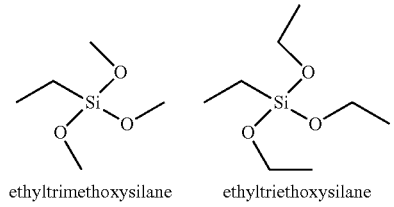

ethyltrimethoxysilane    ethyltriethoxysilane

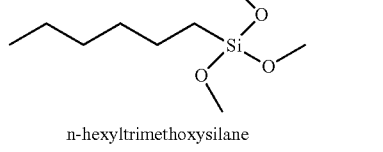

n-hexyltrimethoxysilane

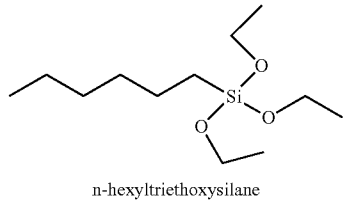

n-hexyltriethoxysilane

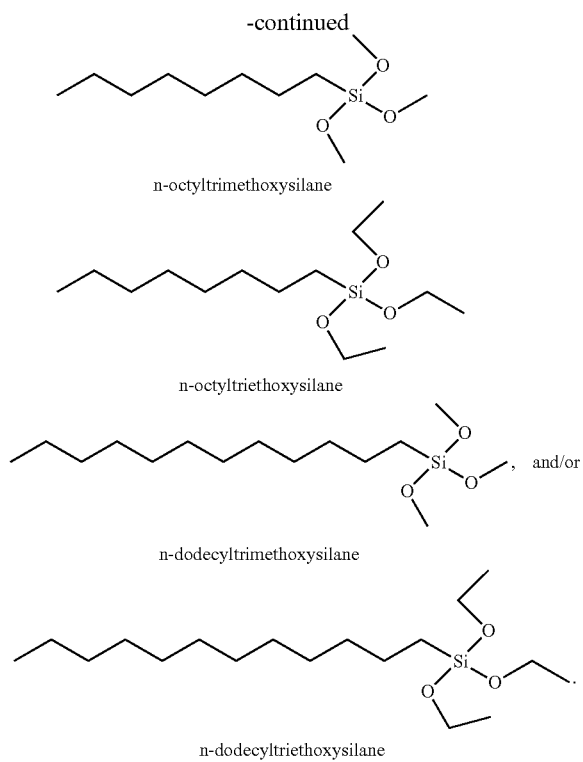

n-octyltrimethoxysilane n-octyltriethoxysilane n-dodecyltrimethoxysilane, and/or n-dodecyltriethoxysilane.

In another preferred embodiment, a method is characterized in that agent (a) contains at least one organosilicon compound (a1) of formula (IV) selected from the group of
methyltrimethoxysilane
methyltriethoxysilane
ethyltrimethoxysilane
ethyltriethoxysilane
propyltrimethoxysilane,
propyltriethoxysilane,
hexyltrimethoxysilane
hexyltriethoxysilane
octyltrimethoxysilane
octyltriethoxysilane
dodecyltrimethoxysilane
dodecyltriethoxysilane
octadecyltrimethoxysilane and/or
octadecyltriethoxysilane.

The organosilicon compounds described above are reactive compounds. In this context, it has been found to be preferable if agent (a) contains one or more organosilicon compounds (a1) in a total amount of from 0.1 to 20 wt %, preferably 1 to 15 wt %, and particularly preferably 2 to 8 wt %, relative to the total weight of agent (a).

In another preferred embodiment, a method is characterized in that agent (a) contains one or more organosilicon compounds (a1) in a total amount of from 0.1 to 20 wt. %, preferably 1 to 15 wt. %, and particularly preferably 2 to 8 wt. %, relative to the total weight of agent (a).

In order to achieve particularly good dyeing results, it is particularly advantageous to use the organosilicon compounds of formula (I) and/or (II) in certain ranges of amounts in the agent (a). Particularly preferably, agent (a) contains one or more organosilicon compounds of formula (I) and/or (II) in a total amount of from 0.1 to 10 wt %, preferably 0.5 to 5 wt %, and particularly preferably 0.5 to 3 wt %, relative to the total weight of agent (a).

In another preferred embodiment, a method is characterized in that agent (a) contains one or more organosilicon compounds of formula (I) and/or (II) in a total amount of from 0.1 to 10 wt. %, preferably 0.5 to 5 wt. %, and particularly preferably 0.5 to 3 wt. %, relative to the total weight of agent (a).

Furthermore, it has been found to be very particularly preferable if the organosilicon compound(s) of formula (IV) are also present in specific quantity ranges in agent (a). Particularly preferably, agent (a) contains one or more organosilicon compounds of formula (IV) in a total amount of from 0.1 to 20 wt %, preferably 2 to 15 wt %, and particularly preferably 4 to 9 wt %, relative to the total weight of agent (a).

In another preferred embodiment, a method is characterized in that agent (a) contains one or more organosilicon compounds of formula (IV) in a total amount of from 0.1 to 20 wt. %, preferably 2 to 15 wt. %, and particularly preferably 3.2 to 10 wt. %, relative to the total weight of agent (a).

In the course of the work leading to this invention, it was found that particularly stable and uniform films could also be obtained on the keratinous material if the agent (a) contains two organosilicon compounds that are structurally different to one another.

In another preferred embodiment, a method is characterized in that agent (a) contains at least two organosilicon compounds that are structurally different to one another.

In a preferred embodiment, a method is characterized in that an agent (a) which contains at least one organosilicon compound of formula (I) and at least one organosilicon compound of formula (IV) is applied on the keratinous material.

In an explicitly very particularly preferred embodiment, a method is characterized in that an agent (a) is applied to the keratinous material, which contains at least one organosilicon compound of formula (I) selected from the group consisting of (3-aminopropyl)triethoxysilane and (3-aminopropyl)trimethoxysilane, and additionally contains at least one organosilicon compound of formula (IV) selected from the group consisting of methyltrimethoxysilane, methyltriethoxysilane, ethyltrimethoxysilane, ethyltriethoxysilane, propyltrimethoxysilane, propyltriethoxysilane, hexyltrimethoxysilane and hexyltriethoxysilane.

In another preferred embodiment, a method is characterized in that agent (a) contains, relative to the total weight of agent (a):
  0.5 to 5 wt % of at least one first organosilicon compound (a1) selected from the group consisting of (3-aminopropyl)trimethoxysilane, (3-aminopropyl)triethoxysilane, (2-aminoethyl)trimethoxysilane, (2-aminoethyl)triethoxysilane, (3-dimethylaminopropyl)trimethoxysilane, (3-dimethylaminopropyl)triethoxysilane, (2-dimethylaminoethyl)trimethoxysilane and (2-dimethylaminoethyl)triethoxysilane, and 3.2 to 10 wt. % of at least one second organosilicon compound (a1) selected from the group consisting of methyltrimethoxysilane, methyltriethoxysilane, ethyltrimethoxysilane, ethyltriethoxysilane, propyltrimethoxysilane, propyltriethoxysilane, hexyltrimethoxysilane, hexyltriethoxysilane, octyltrimethoxysilane, octyltriethoxysilane, dodecyltrimethoxysilane, dodecyltriethoxysilane, octadecyltrimethoxysilane and octadecyltriethoxysilane.

In the context of this embodiment, agent (a) contains one or more organosilicon compounds of a first group in a total amount of 0.5 to 5 wt. %. The organosilicon compounds of this first group are selected from the group consisting of (3-aminopropyl)trimethoxysilane, (3-aminopropyl)triethoxysilane, (2-aminoethyl)trimethoxysilane, (2-aminoethyl)triethoxysilane, (3-dimethylaminopropyl)trimethoxysilane, (3-dimethylaminopropyl)triethoxysilane, (2-dimethylaminoethyl)trimethoxysilane and/or (2-dimethylaminoethyl)triethoxysilane.

In the context of this embodiment, agent (a) contains one or more organosilicon compounds of a second group in a total amount of 3.2 to 10 wt %. The organosilicon compounds of this second group are selected from the group consisting of methyltrimethoxysilane, methyltriethoxysilane, ethyltrimethoxysilane, ethyltriethoxysilane, propyltrimethoxysilane, propyltriethoxysilane, hexyltrimethoxysilane, hexyltriethoxysilane, octyltrimethoxysilane, octyltriethoxysilane, dodecyltrimethoxysilane, dodecyltriethoxysilane, octadecyltrimethoxysilane and octadecyltriethoxysilane.

Even the addition of small amounts of water leads to hydrolysis in the case of organosilicon compounds having at least one hydrolyzable group. The hydrolysis products and/or organosilicon compounds having at least one hydroxy group can react with one another in a condensation reaction. For this reason, both the organosilicon compounds having at least one hydrolyzable group and the hydrolysis and/or condensation products thereof can be present in agent (a). When organosilicon compounds having at least one hydroxyl group are used, both the organosilicon compounds having at least one hydroxyl group and the condensation products thereof can be present in agent (a).

A condensation product is understood to mean a product which results by reaction of at least two organosilicon compounds with at least one hydroxyl group or hydrolyzable groups per molecule with elimination of water and/or with elimination of an alkanol. The condensation products can be, for example, dimers, but also trimers or oligomers, the condensation products being in equilibrium with the monomers. Depending on the amount of water used or consumed in the hydrolysis, the equilibrium of monomeric organosilicon compounds to condensation product shifts.

Very particularly good results were able to be obtained when organosilicon compounds of formula (I) and/or (II) were used in the method. Since, as already described above, hydrolysis/condensation already occurs in the case of traces of moisture, the hydrolysis/condensation products of organosilicon compounds (I) and/or (II) are also covered by this embodiment.

pH of Agent (a)

It has been found to be preferable if the agent (a) is formulated in the form of a water-containing agent that is adjusted to an alkaline pH.

To adjust the pH, the agent (a) can contain at least one alkalizing agent.

To adjust the desired pH, the agents (a) can therefore also contain at least one alkalizing agent. The pH values within the meaning of the present invention are pH values which have been measured at a temperature of 22° C.

Agent (a) may contain, for example, ammonia, alkanolamines and/or basic amino acids as alkalizing agents.

The alkanolamines that can be used in the agent are preferably selected from primary amines having a $C_2$-$C_6$ alkyl parent substance, which carries at least one hydroxyl group. Preferred alkanolamines are selected from the group which is formed of 2-aminoethan-1-ol (monoethanolamine), 3-aminopropan-1-ol, 4-aminobutan-1-ol, 5-amino-pentan-1-ol, 1-aminopropan-2-ol, 1-aminobutan-2-ol, 1-amino-pentan-2-ol, 1-amino-pentan-3-ol, 1-amino-pentan-4-ol, 3-amino-2-methylpropan-1-ol, 1-amino-2-methylpropan-2-ol, 3-aminopropane-1,2-diol, 2-amino-2-methyl propane-1, 3-diol.

Alkanolamines particularly preferred are selected from 2-aminoethan-1-ol and/or 2-amino-2-methylpropan-1-ol. A particularly preferred embodiment is therefore characterized in that the agent contains, as an alkalizing agent, an alkanolamine selected from 2-aminoethan-1-ol and/or 2-amino-2-methylpropan-1-ol.

An amino acid within the meaning of the invention is an organic compound which contains at least one protonatable amino group and at least one —COOH or one —SO$_3$H group in its structure. Preferred amino acids are aminocarboxylic acids, in particular α-(alpha)-aminocarboxylic acids and ω-aminocarboxylic acids, with α-aminocarboxylic acids being particularly preferred.

Basic amino acids are understood to mean the amino acids which have an isoelectric point pI greater than 7.

Basic α-aminocarboxylic acids contain at least one asymmetric carbon atom. In the context of the present invention, both possible enantiomers can equally be used as a specific compound or else mixtures thereof, in particular as racemates. However, it is particularly advantageous to use the naturally occurring isomer form, usually in the L configuration.

The basic amino acids are preferably selected from the group, which is formed of arginine, lysine, ornithine and histidine, more preferably of arginine and lysine. In another particularly preferred embodiment, an agent is therefore characterized in that the alkalizing agent is a basic amino acid from the group of arginine, lysine, ornithine and/or histidine.

Furthermore, the agent can contain additional alkalizing agents, in particular inorganic alkalizing agents. According to the invention, usable, inorganic alkalizing agents are preferably selected from the group, which is formed of sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Very particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Although the agents (a) are preferably set to pH values in the alkaline range, it may nevertheless be necessary in principle to use small amounts of acidifying agents for fine adjustment of the desired pH. Suitable acidifying agents according to the invention are, for example, citric acid, lactic acid, acetic acid or also diluted mineral acids (such as, for example, hydrochloric acid, sulfuric acid, phosphoric acid).

However, in the context of the work leading to this invention, it was found that the presence of the alkalizing agent or the adjustment of the alkaline pH value is essential for the formation of resistant films on the keratinous material. The presence of large amounts of acids can have a negative effect on the strength of the films. For this reason, it has been found to be preferred to minimize the amounts of acids used in agent (a). For this reason, it is advantageous if the total amount of the organic and/or inorganic acids contained in agent (a) does not exceed a certain value.

In a further preferred embodiment, a method is characterized in that the total amount of organic acids from the group consisting of citric acid, tartaric acid, malic acid and lactic acid contained in agent (a) is below 1 wt. %, preferably below 0.7 wt. %, more preferably below 0.5 wt. %, even more preferably below 0.1 wt. % and very particularly preferably below 0.01 wt. %.

In a further preferred embodiment, a method is characterized in that the total amount of inorganic acids from the group consisting of hydrochloric acid, sulfuric acid and phosphoric acid contained in agent (a) is below 1 wt. %, preferably below 0.7 wt. %, more preferably below 0.5 wt. %, even more preferably below 0.1 wt. % and very particularly preferably below 0.01 wt. %.

The above maximum total amounts of the acids contained in agent (a) are always based on the total weight of agent (a).

Agent (b)

In addition to the application of agents (v) and (a), the method for treating keratinous material also comprises the application of agent (b). Agent (b) is characterized in that it contains at least one sealing reagent (b1).

The application of agent (b) to the keratinous material treated with agent (a) results in the colorings obtained in the method being made more durable. In particular, by applying agent (b), the wash-fastness and the resistance to friction of the colorings obtained in the method can be improved.

It is preferable that the sealing reagent (b1) comprises a compound selected from the group consisting of film-forming polymers, alkalizing agents, acidifying agents and mixtures thereof.

It may be preferable that the sealing reagent comprises a film-forming polymer.

Polymers are to be understood as macromolecules which have a molecular weight of at least 1000 g/mol, preferably at least 2500 g/mol, particularly preferably at least 5000 g/mol, and which consist of similar repeating organic units. The polymers of the present invention may be synthetically produced polymers produced by polymerization of one monomer type or by polymerization of various monomer types that are structurally different to one another. If the polymer is prepared by polymerization of one monomer type, it is a homopolymer. If structurally different monomer types are used in the polymerization, the resultant polymer is referred to as a copolymer.

The maximum molecular weight of the polymer depends on the degree of polymerization (number of polymerized monomers) and the size of the batch, and is determined by the polymerization method. In the context of the present invention, it is preferable that the maximum molecular weight of the film-forming polymer as sealing reagent (b1) is not more than $10^7$ g/mol, preferably not more than $10^6$ g/mol, and particularly preferably not more than $10^5$ g/mol.

In the context of the invention, a film-forming polymer means a polymer which is capable of forming a film on a substrate, for example on a keratinous material or a keratinous fiber. The formation of a film can be detected, for example, by observing the keratinous material treated with the polymer under a microscope.

The film-forming polymers (b1) in agent (b) may be hydrophilic or hydrophobic.

In the context of a first embodiment, it may be preferable to use at least one hydrophobic film-forming polymer in agent (b) as sealing reagent (b1).

A hydrophobic polymer means a polymer that has a solubility in water at 25° C. (760 mmHg) of less than 1 wt %.

The water solubility of the film-forming hydrophobic polymer can be determined, for example, in the following way. 1 g of the polymer is added to a beaker. Water is added to 100 g. A stirrer bar is added, and the mixture is heated to 25° C. on a magnetic stirrer, with stirring. Stirring is carried out for 60 minutes. Thereafter, the aqueous mixture is visually assessed. If the polymer-water mixture cannot be visually assessed due to the mixture having a high level of haze, the mixture is filtered. If a proportion of undissolved polymer remains on the filter paper, the solubility of the polymer is less than 1 wt %.

Mention may particularly be made here of polymers of the acrylic acid type, polyurethanes, polyesters, polyamides, polyureas, cellulose polymers, nitrocellulose polymers, silicone polymers, polymers of the acrylamide type and polyisoprenes.

Particularly well-suited film-forming hydrophobic polymers are for example polymers from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

In a further preferred embodiment, an agent (b) is characterized in that it contains at least one film-forming hydrophobic polymer as sealing reagent (b1) selected from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

To achieve the object according to the invention, film-forming hydrophobic polymers selected from the group of synthetic polymers, polymers obtained by radical polymerization, or natural polymers, have proven particularly well-suited.

Further particularly well-suited film-forming hydrophobic polymers can be selected from homopolymers or copolymers of olefins, for example cycloolefins, butadiene, isoprene or styrene, vinyl ethers, vinylamides, esters or amides of (meth)acrylic acid with at least one $C_1$-$C_{20}$ alkyl group, an aryl group or a $C_2$-$C_{10}$ hydroxyalkyl group.

Further film-forming hydrophobic polymers can be selected from the homopolymers or copolymers of isooctyl (meth)acrylate, isononyl(meth)acrylate, 2-ethylhexyl(meth)acrylate, lauryl(meth)acrylate, isopentyl(meth)acrylate, n-butyl(meth)acrylate, isobutyl(meth)acrylate, ethyl(meth)acrylate, methyl(meth)acrylate, tert-butyl(meth)acrylate, stearyl(meth)acrylate, hydroxyethyl(meth)acrylate, 2-hydroxypropyl(meth)acrylate, 3-hydroxypropyl(meth)acrylate and/or mixtures thereof.

Further film-forming hydrophobic polymers can be selected from homopolymers or copolymers of (meth)acrylamide, n-alkyl(meth)acrylamides, in particular those with $C_2$-$C_{18}$ alkyl groups, for example N-ethylacrylamide, n-tert-butylacrylamide, N-octylacrylamide, n-di($C_1$-$C_4$)alkyl (meth)acrylamide.

Further preferred anionic copolymers are, for example, copolymers of acrylic acid, methacrylic acid or the $C_1$-$C_6$ alkyl esters thereof, as are sold under the INCI name Acrylates Copolymers. One suitable commercially available product is Aculyn® 33 from Rohm & Haas, for example. However, further preferred are copolymers of acrylic acid, methacrylic acid or their $C_1$-$C_6$ alkyl esters and the esters of an ethylenically unsaturated acids and an alkoxylated fatty alcohols. Suitable ethylenically unsaturated acids are in particular acrylic acid, methacrylic acid and itaconic acid, and suitable alkoxylated fatty alcohols are in particular Steareth-20 or Ceteth-20.

The most particularly preferred commercially available polymers are, for example, Aculyn® 22 (Acrylates/Steareth-20 Methacrylate Copolymer), Aculyn® 28 (Acrylates/Beheneth-25 Methacrylate Copolymer), Structure 2001® (Acrylates/Steareth-20 Itaconate Copolymer), Structure 3001® (Acrylates/Ceteth-20 Itaconate Copolymer), Structure Plus® (Acrylates/Aminoacrylates C10-30 Alkyl PEG-20 Itaconate Copolymer), Carbopol® 1342, 1382, Ultrez 20, Ultrez 21 (Acrylates/C10-30 Alkyl Acrylate Crosspolymer), Synthalen W 2000® (Acrylates/Palmeth-25 Acrylate Copolymer) or Soltex OPT (Acrylates/C12-22 Alkyl methacrylate Copolymer) sold by Rohme and Haas.

As examples of suitable polymers based on vinyl monomers, mention may be made of homopolymers and copolymers of N-vinylpyrrolidone, of vinylcaprolactam, of vinyl (C1-C6)alkylpyrrole, of vinyloxazole, of vinylthiazole, of vinylpyrimidine or of vinylimidazole.

In addition, the copolymers octylacrylamide/acrylates/butylaminoethyl methacrylate copolymer, as is commercially available, for example, under the trade names AMPHOMER® or LOVOCRYL® 47 by NATIONAL STARCH, or the copolymers of acrylates/octylacrylamides commercially available under the trade names DERMACRYL® LT and DERMACRYL® 79 from NATIONAL STARCH, are very particularly well-suited.

As examples of suitable polymers based on olefins, mention may be made of homopolymers and copolymers of ethylene, of propylene, of butene, of isoprene and of butadiene.

In the context of a further embodiment, block copolymers which comprise at least one block of styrene or derivatives of styrene can be used as film-forming hydrophobic polymers. These block copolymers can be copolymers which, in addition to a styrene block, contain one or more further blocks, for example styrene/ethylene, styrene/ethylene/butylene, styrene/butylene, styrene/isoprene, styrene/butadiene. Corresponding polymers are commercially available from BASF under the trade name "Luvitol HSB".

Surprisingly, it was found that very particularly intense and wash-fast colorings could be obtained if agent (b) contained, as sealing reagent (b1), at least one film-forming polymer selected from the group of homopolymers and copolymers of acrylic acid, homopolymers and copolymers of methacrylic acid, homopolymers and copolymers of acrylic acid esters, homopolymers and copolymers of methacrylic acid esters, homopolymers and copolymers of acrylic acid amides, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, of polyurethanes, of polyesters and of polyamides.

In a further preferred embodiment, a method is characterized in that agent (b) contains, as sealing reagent (b1), at least one film-forming polymer selected from the group of homopolymers and copolymers of acrylic acid, homopolymers and copolymers of methacrylic acid, homopolymers and copolymers of acrylic acid esters, homopolymers and copolymers of methacrylic acid esters, homopolymers and copolymers of acrylic acid amides, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, of polyurethanes, of polyesters and of polyamides.

In the context of a further embodiment, it may be preferable to use at least one hydrophilic film-forming polymer in agent (b) as sealing reagent (b1).

A hydrophilic polymer means a polymer that has a solubility in water at 25° C. (760 mmHg) of more than 1 wt %, preferably more than 2 wt %.

The water solubility of the film-forming hydrophilic polymer can be determined, for example, in the following way. 1 g of the polymer is added to a beaker. Water is added to 100 g. A stirrer bar is added, and the mixture is heated to 25° C. on a magnetic stirrer, with stirring. Stirring is carried out for 60 minutes. Thereafter, the aqueous mixture is visually assessed. A completely dissolved polymer appears macroscopically homogeneous. If the polymer-water mixture cannot be visually assessed due to the mixture having a high level of haze, the mixture is filtered. If no undissolved polymer remains on the filter paper, the solubility of the polymer is more than 1 wt %.

Non-ionic, anionic and cationic polymers can be used as film-forming hydrophilic polymers.

Suitable film-forming hydrophilic polymers can be selected, for example, from the group of polyvinylpyrrolidone (co)polymers, polyvinyl alcohol (co)polymers, vinyl acetate (co)polymers, carboxyvinyl (co)polymers, acrylic acid (co)polymers, methacrylic acid (co)polymers, natural gums, polysaccharides and/or acrylamide (co)polymers.

Furthermore, it is very particularly preferable to use polyvinylpyrrolidone (PVP) and/or a copolymer containing vinylpyrrolidone as the film-forming hydrophilic polymer.

In a further very particularly preferred embodiment, an agent (b) is characterized in that it contains at least one film-forming hydrophilic polymer as sealing reagent (b1) selected from the group of polyvinylpyrrolidone (PVP) and the copolymers of polyvinylpyrrolidone.

It is further preferred if the agent comprises polyvinylpyrrolidone (PVP) as the film-forming hydrophilic polymer. Surprisingly, the wash-fastness of the colorings that could be obtained with PVP-containing agents (b) was also very good.

Particularly well-suited polyvinylpyrrolidones are available, for example, under the name Luviskol® K from BASF SE, in particular Luviskol® K 90 or Luviskol® K 85 from BASF SE.

As a further explicitly particularly well-suited polyvinylpyrrolidone (PVP), the polymer PVP K30 which is sold by Ashland (ISP, POI Chemical) can also be used. PVP K 30 is a polyvinylpyrrolidone which is highly soluble in cold water and has the CAS number 9003-39-8. The molar weight of PVP K 30 is approximately 40,000 g/mol.

Further very particularly well-suited polyvinylpyrrolidones are the substances known under the trade names LUVITEC K 17, LUVITEC K 30, LUVITEC K 60, LUVITEC K 80, LUVITEC K 85, LUVITEC K 90 and LUVITEC K 115, which are available from BASF.

The use of film-forming hydrophilic polymers from the group of copolymers of the polyvinylpyrrolidone as sealing reagent (b1) likewise has led to particularly good and wash-resistant dyeing results.

As particularly well-suited film-forming hydrophilic polymers, in this context, mention may be made of vinylpyrrolidone-vinyl ester copolymers, as are for example sold under the trade name Luviskol® (BASF). Luviskol® VA 64 and Luviskol® VA 73, each being vinylpyrrolidone/vinyl acetate copolymers, are particularly preferred nonionic polymers.

Among the vinylpyrrolidone-containing copolymers, very particular preference is given to using a styrene/VP copolymer and/or a vinylpyrrolidone-vinyl acetate copolymer and/or a VP/DMAPA Acrylates Copolymer and/or a VP/vinyl caprolactam/DMAPA Acrylates Copolymer in the cosmetic compositions.

Vinylpyrrolidone-vinyl acetate copolymers are sold under the name Luviskol® VA from BASF SE. A VP/vinyl caprolactam/DMAPA Acrylates Copolymer is sold, for example, under the trade name Aquaflex® SF-40 from Ashland Inc. A VP/DMAPA Acrylates Copolymer is sold, for example, under the name Styleze CC-10 by Ashland and is a highly preferred vinylpyrrolidone-containing copolymer.

As further suitable copolymers of polyvinylpyrrolidone, mention may also be made of the copolymers obtained by reacting N-vinylpyrrolidone with at least one further monomer from the group of V-vinylformamide, vinyl acetate, ethylene, propylene, acrylamide, vinylcaprolactam, vinylcaprolactone and/or vinyl alcohol.

In a further very particularly preferred embodiment, an agent (b) is characterized in that it contains at least one film-forming hydrophilic polymer as sealing reagent (b1) selected from the group of polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers.

A further suitable copolymer of vinylpyrrolidone is the polymer known under the INCI name Maltodextrin/VP Copolymer.

Furthermore, it was possible to obtain intensely-colored keratinous material, in particular hair, with very good washfastness when a nonionic film-forming hydrophilic polymer was used as the film-forming hydrophilic polymer.

In the context of a further embodiment, agent (b) can contain at least one nonionic film-forming hydrophilic polymer as sealing reagent (b1).

According to the invention, a nonionic polymer is understood to be a polymer that, in a protic solvent—for example water—under standard conditions, bears no structural units having permanently cationic or anionic groups which would have to be compensated by counterions to maintain electroneutrality. Quaternized ammonium groups, for example, fall under cationic groups, but protonated amines do not. Carboxyl groups and sulfonic acid groups, for example, fall under anionic groups.

Very particular preference is given to agents which contain, as nonionic film-forming hydrophilic polymer, at least one polymer selected from the group of polyvinylpyrrolidone,
copolymers of N-vinylpyrrolidone and vinyl esters of carboxylic acids having 2 to 18 carbon atoms, in particular of N-vinylpyrrolidone and vinyl acetate,
copolymers of N-vinylpyrrolidone and N-vinylimidazole and methacrylamide,
copolymers of N-vinylpyrrolidone and N-vinylimidazole and acrylamide,
copolymers of N-vinylpyrrolidone with N,N-di(C1 to C4)alkylamino-(C2 to C4)alkylacrylamide.

If copolymers of N-vinylpyrrolidone and vinyl acetate are used, it is again preferred if the molar ratio of the polymer structural units containing the N-vinylpyrrolidone monomer to the polymer structural units containing the vinyl acetate monomer is in the range from 20 to 80 to 80 to 20, in particular from 30 to 70 to 60 to 40. Suitable copolymers of vinylpyrrolidone and vinyl acetate are available, for example, under the trade names Luviskol® VA 37, Luviskol® VA 55, Luviskol® VA 64 and Luviskol® VA 73 from BASE SE.

A further particularly preferred polymer is selected from the polymers having the INCI name VP/Methacrylamide/Vinyl Imidazole Copolymer, which are available, for example, from BASE SE under the trade name Luviset Clear.

A further very particularly preferred nonionic film-forming hydrophilic polymer is a copolymer of N-vinylpyrrolidone and N,N-dimethylaminopropylmethacrylamide, which is sold, for example, with the INCI name VP/DMAPA Acrylates Copolymer, for example under the trade name Styleze® CC 10 from ISP.

A cationic polymer is the copolymer of N-vinylpyrrolidone, N-vinylcaprolactam, N-(3-dimethylaminopropyl) methacrylamide and 3-(methacryloylamino)propyl-lauryl dimethylammonium chloride (INCI name: Polyquaternium-69), which is marketed, for example, under the trade name AquaStyle® 300 (28-32 wt. % active substance in an ethanol-water mixture, molecular weight 350000) by the company ISP.

Further suitable film-forming hydrophilic polymers are, for example
vinylpyrrolidone-vinylimidazolium methochloride copolymers, as sold under the names Luviquat® FC 370, FC 550 and the INCI name Polyquaternium-16 and also FC 905 and HM 552,
vinylpyrrolidone-vinylcaprolactam-acrylate terpolymers, as are commercially available, for example, under the name Aquaflex® SF 40 with acrylic acid esters and acrylic acid amides as third monomer building blocks.

Polyquaternium-11 is the reaction product of diethyl sulfate with a copolymer of vinylpyrrolidone and dimethylaminoethyl methacrylate. Suitable commercial products are available, for example, under the names Dehyquart® CC 11 and Luviquat® PQ 11 PN from BASF SE or Gafquat 440, Gafquat 734, Gafquat 755 or Gafquat 755N from Ashland Inc.

Polyquaternium-46 is the reaction product of vinylcaprolactam and vinylpyrrolidone with methylvinylimidazolium methosulfate and is available, for example, under the name Luviquat® Hold from BASF SE. Polyquaternium-46 is preferably used in an amount of 1 to 5 wt % relative to the total weight of the cosmetic composition. It is very particularly preferable that Polyquaternium-46 is used in combination with a cationic guar compound. It is even most highly preferable that Polyquaternium-46 is used in combination with a cationic guar compound and Polyquaternium-11.

As suitable anionic film-forming hydrophilic polymers, use can for example be made of acrylic acid polymers which may be present in uncrosslinked or crosslinked form. Corresponding products are commercially available, for example, under the trade names Carbopol 980, 981, 954, 2984 and 5984 from Lubrizol or else under the names Synthalen M and Synthalen K from 3V Sigma (The Sun Chemicals, Inter Harz).

Examples of suitable film-forming hydrophilic polymers from the group of natural gums are xanthan gum, gellan gum and carob gum.

Examples of suitable film-forming hydrophilic polymers from the group of polysaccharides are hydroxyethyl cellulose, hydroxypropyl cellulose, ethyl cellulose and carboxymethyl cellulose.

Suitable film-forming hydrophilic polymers from the group of the acrylamides are, for example, polymers which are prepared starting from monomers of (meth)acrylamido-C1-C4-alkylsulfonic acid or the salts thereof. Corresponding polymers can be selected from the polymers of polyacrylamidomethanesulfonic acid, polyacrylamidoethanesulfonic acid, polyacrylamidopropanesulfonic acid, poly-2-acrylamido-2-methylpropanesulfonic acid, poly-2-methylacrylamido-2-methylpropanesulfonic acid and/or poly-2-methylacrylamido-n-butanesulfonic acid.

Preferred polymers of poly(meth)arylamido-C1-C4-alkylsulfonic acids are crosslinked and neutralized to at least 90%. These polymers can be crosslinked or else uncrosslinked.

Crosslinked and completely or partially neutralized polymers of the type of the poly-2-acrylamido-2-methylpropanesulfonic acids are known under the INCI names "Ammonium Polyacrylamido-2-methyl-propanesulphonate" or "Ammonium Polyacryldimethyltauramide".

Another preferred polymer of this type is the cross-linked poly-2-acrylamido-2-methyl-propaneulphonic acid polymer marketed by the company Clariant under the trade name Hostacerin AMPS, which is partially neutralized with ammonia.

In a further explicitly very particularly preferred embodiment, a method is characterized in that agent (b) contains at least one anionic film-forming polymer as sealing reagent (b1).

In this context, it was possible to achieve the best results if agent (b) contains, as sealing reagent (b1), at least one film-forming polymer which comprises at least one structural unit of formula (P-I) and at least one structural unit of formula (P-II)

wherein
M represents a hydrogen atom or ammonium (NH$_4$), sodium, potassium, ½ magnesium or ½ calcium.

In a further preferred embodiment, a method is characterized in that agent (b) contains, as sealing reagent (b1), at least one film-forming polymer which comprises at least one structural unit of formula (P-I) and at least one structural unit of formula (P-II)

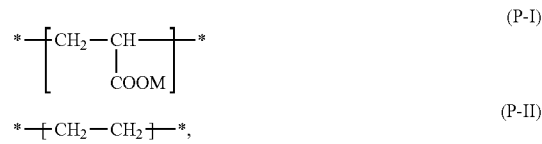

wherein
M represents a hydrogen atom or ammonium (NH$_4$), sodium, potassium, ½ magnesium or ½ calcium.

If M is a hydrogen atom, the structural unit of formula (P-I) is based on an acrylic acid unit.

If M is an ammonium counterion, the structural unit of formula (P-I) is based on the ammonium salt of acrylic acid.

If M is a sodium counterion, the structural unit of formula (P-I) is based on the sodium salt of acrylic acid.

If M is a potassium counterion, the structural unit of formula (P-I) is based on the potassium salt of acrylic acid.

If M is a half equivalent of a magnesium counterion, the structural unit of formula (P-I) is based on the magnesium salt of acrylic acid.

If M is a half equivalent of a calcium counterion, the structural unit of formula (P-I) is based on the calcium salt of acrylic acid.

The film-forming polymer(s) (b1) are preferably used in specific quantity ranges in agent (b). In this context, in order to achieve the object of the invention, it has proven particularly preferable if agent (b) contains one or more film-forming polymers as sealing reagent (b1) in a total amount of 0.1 to 18 wt %, preferably 1 to 16 wt %, more preferably 5 to 14.5 wt %, and most particularly preferably 8 to 12 wt %, relative to the total weight of agent (b).

In a further preferred embodiment, a method is characterized in that agent (b) contains one or more film-forming polymers as sealing reagent (b1) in a total amount of 0.1 to 18 wt. %, preferably 1 to 16 wt. %, more preferably 5 to 14.5 wt. %, and most particularly preferably 8 to 12 wt. %, relative to the total weight of agent (b).

The application of agent (b), comprising a film-forming polymer as sealing reagent (b1), is intended to seal and/or fix the optionally colored film produced initially by the application of agent (a). By applying the second agent (b) with a film-forming polymer as a sealing reagent (b1), the film-forming polymer (b1) is deposited in the form of a further film on the optionally colored film produced in the first layer. If agent (b) further contains at least one dyeing compound, the color impression of a colored film produced in the first step is intensified or modified depending on the dyeing compound used or a coloration of the treated keratinous material is obtained by forming a second colored film on a first uncolored film. The multilayer film system produced in this way has improved resistance to external influences.

In an alternative embodiment, the sealing reagent (b1) contains an alkalizing agent.

Particularly preferably, the alkalizing agent is selected from the group consisting of ammonia, C$_2$-C$_6$ alkanolamines, basic amino acids, alkali metal hydroxides and alkaline earth metal hydroxides.

In the context of a further particularly preferred embodiment, a method is characterized in that agent (b) contains, as sealing reagent (b1), at least one alkalizing agent selected from the group of ammonia, C$_2$-C$_6$ alkanolamines, basic amino acids, alkali metal hydroxides, alkaline earth metal hydroxides, alkali metal silicates, alkali metal metasilicates, alkaline earth metal silicates, alkaline earth metal metasilicates, alkali metal carbonates and alkaline earth metal carbonates.

It has been found that the post-treatment with an agent (b) containing ammonia has a particularly good influence on improving the wash-fastness and the friction-fastness of the colorings obtained in the method.

In the context of a further, very particularly preferred embodiment, a method is characterized in that composition (b) contains ammonia as sealing reagent (b1).

It was also possible to achieve good results if, as sealing reagent (b1), composition (b) contained at least one $C_2$-$C_6$ alkanolamine.

The alkanolamines that can be used in composition (b) can preferably be selected from the group of primary amines having a $C_2$-$C_6$ alkyl underlying structure bearing at least one hydroxyl group. Preferred alkanolamines are selected from the group which is formed of 2-aminoethan-1-ol (monoethanolamine), 3-aminopropan-1-ol, 4-aminobutan-1-ol, 5-amino-pentan-1-ol, 1-aminopropan-2-ol, 1-aminobutan-2-ol, 1-amino-pentan-2-ol, 1-amino-pentan-3-ol, 1-amino-pentan-4-ol, 3-amino-2-methylpropan-1-ol, 1-amino-2-methylpropan-2-ol, 3-aminopropane-1,2-diol and 2-amino-2-methyl propane-1,3-diol.

In a further preferred embodiment, a method according to the invention is characterized in that composition (b) contains, as sealing reagent (b1), at least one alkalizing agent from the group of alkanolamines, that is preferably selected from the group of 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol and 2-amino-2-methylpropane-1,3-diol.

It was also possible to achieve good results if, as sealing reagent (b1), composition (b) contained at least one basic amino acid.

An amino acid within the meaning of the invention is an organic compound which contains at least one protonatable amino group and at least one —COOH or one —$SO_3H$ group in its structure. Preferred amino acids are aminocarboxylic acids, in particular α-(alpha)-amino-carboxylic acids and ω-aminocarboxylic acids, with α-aminocarboxylic acids being particularly preferred.

According to the invention, basic amino acids are understood to mean the amino acids which have an isoelectric point pI greater than 7.0.

Basic α-aminocarboxylic acids contain at least one asymmetric carbon atom. In the context of the present invention, both possible enantiomers can equally be used as a specific compound or else mixtures thereof, in particular as racemates. However, it is particularly advantageous to use the naturally occurring isomer form, usually in the L configuration.

The basic amino acids are preferably selected from the group, which is formed of arginine, lysine, ornithine and histidine, more preferably of arginine and lysine. In another particularly preferred embodiment, the method is therefore characterized in that sealing reagent (b1) is an alkalizing agent, comprising a basic amino acid from the group of arginine, lysine, ornithine and/or histidine.

In a further preferred embodiment, the method is characterized in that agent (b) contains, as sealing reagent (b1), at least one alkalizing agent from the group of basic amino acids, preferably selected from the group of arginine, lysine, ornithine and histidine.

It was also possible to achieve good results if, as sealing reagent (b1), composition (b) contains at least one alkali metal hydroxide. Mention may be made, as examples of well-suited alkali metal hydroxides, of sodium hydroxide and potassium hydroxide.

It was also possible to achieve good results if, as sealing reagent (b1), composition (b) contained an alkalizing agent comprising at least one alkaline earth metal hydroxide. Mention may be made, as examples of well-suited alkaline earth metal hydroxides, of magnesium hydroxide, calcium hydroxide and barium hydroxide.

It was also possible to achieve good results if, as sealing reagent (b1), agent (b) contained at least one alkali metal silicate and/or alkali metal metasilicate. Suitable alkali metal silicates are, for example, sodium silicate and potassium silicate. Suitable alkali metal metasilicates are, for example, sodium metasilicate and potassium metasilicate.

It was also possible to achieve good results if, as sealing reagent (b1), agent (b) contained at least one alkali metal carbonate and/or alkaline earth metal carbonate. Suitable alkali metal carbonates are, for example, sodium carbonate and potassium carbonate. Suitable alkaline earth metal carbonates are, for example, magnesium carbonate and calcium carbonate.

Within the group of the aforementioned sealing reagent (b1) in the form of an alkalizing agent, ammonia, $C_2$-$C_6$ alkanolamines, basic amino acids and alkali metal hydroxides have proven to be particularly well-suited.

In the context of a further particularly preferred embodiment, the method is characterized in that agent (b) comprises, as sealing reagent (b1), at least one alkalizing agent selected from the group of ammonia, $C_2$-$C_6$ alkanolamines, basic amino acids and alkali metal hydroxides.

In the context of a further particularly preferred embodiment, the method is characterized in that composition (b) contains, as sealing reagent (b1), at least one alkalizing agent selected from the group of ammonia, 2-aminoethan-1-ol, 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropane-1,3-diol, arginine, lysine, ornithine, histidine, sodium hydroxide and potassium hydroxide.

Agent (b) contains the alkalizing agent as a sealing reagent (b1) in a cosmetic carrier, preferably in an aqueous cosmetic carrier.

In this context, it has been found to be preferable if agent (b) contains 5.0 to 99.0 wt %, preferably 15.0 to 97.0 wt %, more preferably 25.0 to 97.0 wt %, even more preferably 35.0 to 97.0 wt %, and very particularly preferably 45.0 to 97.0 wt % of water, relative to the total weight of agent (b).

In the context of a further embodiment, the method is characterized in that agent (b) contains 5.0 to 99.0 wt %, preferably 15.0 to 97.0 wt %, more preferably 25.0 to 97.0 wt %, even more preferably 35.0 to 97.0 wt %, and very particularly preferably 45.0 to 97.0 wt % of water, relative to the total weight of agent (b).

The alkalizing agents contained in agent (b) influence the pH of agent (b). It has been found here that particular alkaline pH values have an advantageous effect on the coloring power that can be achieved in the method and on the fastness properties of the colorings.

For this reason, it is preferable that agent (b), comprising an alkalizing agent as sealing reagent (b1), has a pH of 7.0 to 12.0, preferably 7.5 to 11.5, more preferably 8.0 to 11.0, and very particularly preferably 8.5 to 9.5.

The pH can be measured using customary methods known from the prior art, for example pH measurement by means of glass electrodes, by combination electrodes or by pH indicator paper.

In a further very particularly preferred embodiment, the method is characterized in that agent (b) contains an alkalizing agent as sealing reagent (b1) and has a pH of 7.0 to 12.0, preferably 7.5 to 11.5, more preferably 8.0 to 11.0, and very particularly preferably 8.5 to 9.5.

The pH values within the meaning of the present invention are pH values which have been measured at a temperature of 22° C.

In yet another alternative embodiment, the sealing reagent (b1) contains an acidifying agent.

Particularly preferably, the acidifying agent is selected from the group consisting of inorganic acids, organic acids and mixtures thereof.

It was possible to achieve good results if, as sealing reagent (b1), composition (b) contains at least one inorganic acid. Suitable inorganic acids are, for example, phosphoric acid, sulfuric acid and/or hydrochloric acid, particular preference being given to sulfuric acid.

In a further preferred embodiment, the method is characterized in that agent (b) contains, as sealing reagent (b1), at least one acidifying agent from the group of inorganic acids, which is preferably selected from the group consisting of phosphoric acid, sulfuric acid, hydrochloric acid and mixtures thereof.

In the context of a further, even more preferred embodiment, the method is characterized in that agent (b) contains sulfuric acid as sealing reagent (b1).

It was also possible to achieve good results if, as sealing reagent (b1), agent (b) contains at least one organic acid. The organic acid is preferably selected from the group consisting of formic acid, acetic acid, propionic acid, butyric acid, isobutyric acid, valeric acid, isovaleric acid, pivalic acid, oxalic acid, malonic acid, succinic acid, glutaric acid, glyceric acid, glyoxylic acid, adipic acid, pimelic acid, suberic acid, azelaic acid, sebacic acid, propiolic acid, crotonic acid, isocrotonic acid, elaidic acid, maleic acid, fumaric acid, muconic acid, citraconic acid, mesaconic acid, camphoric acid, benzoic acid, o, m, p-phthalic acid, naphthoic acid, toluic acid, hydratropic acid, atropic acid, cinnamic acid, isonicotinic acid, nicotinic acid, bicarbaminic acid, 4,4'-dicyano-6,6'-binicotinic acid, 8-carbamoyloctanic acid, 1,2,4-pentanetricarboxylic acid, 2-pyrrole carboxylic acid, 1,2,4,6,7-naphthalene pentaacetic acid, malonaldehydic acid, 4-hydroxyphthalamidic acid, 1-pyrazolecarboxylic acid, gallic acid or propanetricarboxylic acid, glycolic acid, gluconic acid, lactic acid, maleic acid, ascorbic acid, malic acid, tartaric acid, citric acid and mixtures thereof.

In a further preferred embodiment, the method is characterized in that agent (b) contains, as sealing reagent (b1), at least one acidifying agent from the group of the organic acids, wherein the organic acid is preferably selected from the group consisting of formic acid, acetic acid, propionic acid, butyric acid, isobutyric acid, valeric acid, isovaleric acid, pivalic acid, oxalic acid, malonic acid, succinic acid, glutaric acid, glyceric acid, glyoxylic acid, adipic acid, pimelic acid, suberic acid, azelaic acid, sebacic acid, propiolic acid, crotonic acid, isocrotonic acid, elaidic acid, maleic acid, fumaric acid, muconic acid, citraconic acid, mesaconic acid, camphoric acid, benzoic acid, o,m,p-phthalic acid, naphthoic acid, toluic acid, hydratropic acid, atropic acid, cinnamic acid, isonicotinic acid, nicotinic acid, bicarbaminic acid, 4,4'-dicyano-6,6'-binicotinic acid, 8-carbamoyloctanic acid, 1,2,4-pentanetricarboxylic acid, 2-pyrrole carboxylic acid, 1,2,4,6,7-naphthalene pentaacetic acid, malonaldehydic acid, 4-hydroxyphthalamidic acid, 1-pyrazolecarboxylic acid, gallic acid or propanetricarboxylic acid, glycolic acid, gluconic acid, lactic acid, maleic acid, ascorbic acid, malic acid, tartaric acid, citric acid and mixtures thereof.

In the context of a further, even more preferred embodiment, the method is characterized in that agent (b) contains acetic acid as sealing reagent (b1).

Likewise suitable acidifying agents include methanesulfonic acid and/or 1-hydroxyethane-1,1-diphosphonic acid.

Within the group of the aforementioned sealing reagents (b1) in the form of an acidifying agent, sulfuric acid and/or acetic acid have proven to be particularly well-suited.

In the context of a further particularly preferred embodiment, the method is characterized in that agent (b) comprises, as sealing reagent (b1), at least one acidifying agent selected from the group of sulfuric acid, acetic acid and mixtures thereof.

Agent (b) contains the acidifying agent as a sealing reagent (b1) in a cosmetic carrier, preferably in an aqueous cosmetic carrier.

The acidifying agents contained in agent (b) influence the pH of agent (b). It has been found here that acid pH values also have an advantageous effect on the coloring power that can be achieved in the method and on the fastness properties of the colorings.

For this reason, it is preferable that agent (b), comprising an acidifying agent as sealing reagent (b1), has a pH of 2.0 to 6.5, preferably 3.0 to 6.0, more preferably 4.0 to 6.0, and very particularly preferably 4.5 to 5.5.

The pH can be measured using customary methods known from the prior art, for example pH measurement by means of glass electrodes, by combination electrodes or by pH indicator paper.

In a further very particularly preferred embodiment, the method is characterized in that agent (b) contains an acidifying agent as sealing reagent (b1) and has a pH of 2.0 to 6.5, preferably 3.0 to 6.0, more preferably 4.0 to 6.0, and very particularly preferably 4.5 to 5.5.

The pH values within the meaning of the present invention are pH values which have been measured at a temperature of 22° C.

Further Ingredients in Agents (a) and (b)

The agents (a) and (b) described above may further comprise one or more optional ingredients. However, it is essential to the invention that at least one of agents (a) and (b) further contains at least one dyeing compound from the group consisting of pigments and/or direct dyes.

It may be preferable that agent (a), in addition to the at least one organosilicon compound from the group of silanes having one, two or three silicon atoms (a1), further comprises at least one dyeing compound selected from the group consisting of pigments and/or direct dyes.

Alternatively, it may be preferable that agent (b), in addition to the sealing reagent (b1), further comprises at least one dyeing compound selected from the group consisting of pigments and/or direct dyes.

In a likewise preferred embodiment of the method, agent (a) and agent (b) each further comprise at least one dyeing compound selected from the group consisting of pigments and/or direct dyes.

Irrespective of agent (a) and/or (b), the use of pigments in this context has proven to be very particularly preferable.

In a further very particularly preferred embodiment, a method is characterized in that agent (a) and/or agent (b) further contains at least one dyeing compound from the group of the pigments.

Pigments within the meaning of the present invention are understood to mean dyeing compounds which have a solubility of less than 0.5 g/L, preferably of less than 0.1 g/L, even more preferably of less than 0.05 g/L, at 25° C. in water. The water solubility can be determined, for example, by means of the method described below: 0.5 g of the pigment is weighed into a beaker. A stir bar is added. Then one liter of distilled water is added. This mixture is heated to 25° C. while stirring with a magnetic stirrer for one hour. If still undissolved components of the pigment are visible in the mixture after this period, the solubility of the pigment is below 0.5 g/L. If the pigment-water mixture cannot be visually assessed due to the high intensity of the pigment that may be finely dispersed, the mixture is filtered. If a portion of undissolved pigments remains on the filter paper, the solubility of the pigment is below 0.5 g/L.

Suitable pigments may be of inorganic and/or organic origin.

In a preferred embodiment, a method is characterized in that agent (a) and/or agent (b) further comprises at least one dyeing compound from the group of inorganic and/or organic pigments.

Preferred pigments are selected from synthetic or natural inorganic pigments. Inorganic pigments of natural origin can be produced, for example, from chalk, ocher, umber, green earth, burnt Sienna or graphite. Furthermore, black pigments, for example iron oxide black, chromatic pigments, for example ultramarine or iron oxide red, and also fluorescent or phosphorescent pigments, can be used as inorganic color pigments.

Colored metal oxides, hydroxides and oxide hydrates, mixed phase pigments, sulfur-containing silicates, silicates, metal sulfides, complex metal cyanides, metal sulfates, chromates and/or molybdates are particularly suitable. Particularly preferred pigments are black iron oxide (CI 77499), yellow iron oxide (CI 77492), red and brown iron oxide (CI 77491), manganese violet (CI 77742), ultramarine (sodium aluminum sulfosilicates, CI 77007, Pigment Blue 29), chromium oxide hydrate (CI 77289), Iron Blue (ferric ferrocyanide, CI 77510) and/or carmine (cochineal).

Pigments which are likewise particularly preferred are colored pearlescent pigments. These are usually based on mica and may be coated with one or more metal oxides. Mica is a phyllosilicate. The most important representatives of these silicates are muscovite, phlogopite, paragonite, biotite, lepidolite, and margarite. In order to produce the pearlescing pigments in conjunction with metal oxides, mica, primarily muscovite or phlogopite, is coated with a metal oxide.

Accordingly, a preferred method is characterized in that agent (a) and/or agent (b) further contains at least one dyeing compound from the group of pigments selected from the group of colored metal oxides, metal hydroxides, metal oxide hydrates, silicates, metal sulfides, complex metal cyanides, metal sulfates, bronze pigments and/or from colored pigments based on natural or synthetic mica which are coated with at least one metal oxide and/or a metal oxychloride.

In another preferred embodiment, the method is characterized in that agent (a) and/or agent (b) contains at least one dyeing compound from the group of pigments selected from pigments based on natural or synthetic mica which are coated with one or more metal oxides from the group of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, pigment blue 29), chromium oxide hydrate (CI 77289), chromium oxide (CI 77288) and/or iron blue (ferric ferrocyanide, CI 77510).

Other suitable pigments are based on metal oxide-coated platelet-shaped borosilicate. These are coated, for example, with tin oxide, iron oxide(s), silicon dioxide and/or titanium dioxide. Such borosilicate-based pigments are available, for example, under the name MIRAGE from Eckart or Reflecks from BASF SE.

In a preferred embodiment, agent (a) is characterized in that it contains at least one dyeing compound from the group of inorganic pigments selected from the group consisting of black iron oxide (CI 77499), yellow iron oxide (CI 77492), red iron oxide (CI 77491) and mixtures thereof.

Yellow iron oxide (or also iron oxide yellow) is the name for FeO(OH), listed in the Color Index under C.I. Pigment Yellow 42.

Red iron oxide (or also iron oxide red) is the name for $Fe_2O_3$, listed in the Color Index under C.I. Pigment Red 101. Depending on the particle size, red iron oxide pigments can be adjusted to have from a very yellow tint (small particle size) to a very blue tint (coarse particles).

Black iron oxide (or also iron oxide black) is listed in the Colour Index under C.I. Pigment Black 11. Iron oxide black is ferromagnetic. The chemical formula is commonly stated as $Fe_3O_4$, but in reality a mixed crystal of $Fe_2O_3$ and FeO with an inverse spinel structure is present. By doping with chromium, copper or manganese, further black pigments are obtained.

Brown black iron oxide (or also iron oxide brown) usually does not refer to a defined pigment but a mixture of yellow, red and/or black iron oxide.

Iron oxide pigments typically have particle diameters in the range from 2000 to 4000 nm. For some applications, in particular for cosmetic purposes, it may be advantageous to use iron oxide pigments with considerably smaller particle diameters. Thus, hair colorings with iron oxide pigments having a particle diameter in the range from 100 to 1000 nm, more preferably 150 nm 700 nm, show better durability and better gray coverage.

Therefore, even more preferred is an agent (a) which further comprises a dyeing compound from the group of pigments and/or direct dyes, wherein the dyeing compound comprises a pigment from the group of iron oxide pigments, and wherein the iron oxide pigment has a particle diameter in the range from 100 to 1000 nm, more preferably 150 nm 700 nm.

Examples of particularly suitable color pigments are commercially available, for example, under the trade names Rona®, Colorona®, Xirona®, Dichrona® and Timiron® from Merck, Ariabel® and Unipure® from Sensient, Prestige® or SynCrystal from Eckart Cosmetic Colors, Flamenco®, Cellini®, Cloisonné®, Duocrome®, Gemtone®, Timica®, MultiReflections, Chione from BASF SE and Sunshine® from Sunstar.

Very particularly preferred pigments with the trade name Colorona® are, for example:
Colorona Copper, Merck, MICA, CI 77491 (IRON OXIDES)
Colorona Copper Fine, Merck, MICA, CI 77491 (IRON OXIDES)
Colorona Passion Orange, Merck, Mica, CI 77491 (IRON OXIDES), Alumina Colorona Patina Silver, Merck, MICA, CI 77499 (IRON OXIDES), CI 77891 (TITANIUM DIOXIDE)
Colorona RY, Merck, CI 77891 (TITANIUM DIOXIDE), MICA, CI 75470 (CARMINE)
Colorona Oriental Beige, Merck, MICA, CI 77891 (TITANIUM DIOXIDE), CI 77491 (IRON OXIDES)
Colorona Dark Blue, Merck, MICA, TITANIUM DIOXIDE, FERRIC FERROCYANIDE
Colorona Chameleon, Merck, CI 77491 (IRON OXIDES), MICA
Colorona Aborigine Amber, Merck, MICA, CI 77499 (IRON OXIDES), CI 77891 (TITANIUM DIOXIDE)
Colorona Blackstar Blue, Merck, CI 77499 (IRON OXIDES), MICA
Colorona Patagonian Purple, Merck, MICA, CI 77491 (IRON OXIDES), CI 77891 (TITANIUM DIOXIDE), CI 77510 (FERRIC FERROCYANIDE)
Colorona Red Brown, Merck, MICA, CI 77491 (IRON OXIDES), CI 77891 (TITANIUM DIOXIDE)
Colorona Russet, Merck, CI 77491 (TITANIUM DIOXIDE), MICA, CI 77891 (IRON OXIDES)
Colorona Imperial Red, Merck, MICA, TITANIUM DIOXIDE (CI 77891), D&C RED NO. 30 (CI 73360)
Colorona Majestic Green, Merck, CI 77891 (TITANIUM DIOXIDE), MICA, CI 77288 (CHROMIUM OXIDE GREENS)
Colorona Light Blue, Merck, MICA, TITANIUM DIOXIDE (CI 77891), FERRIC FERROCYANIDE (CI 77510)
Colorona Red Gold, Merck, MICA, CI 77891 (TITANIUM DIOXIDE), CI 77491 (IRON OXIDES)
Colorona Gold Plus MP 25, Merck, MICA, TITANIUM DIOXIDE (CI 77891), IRON OXIDES (CI 77491)
Colorona Carmine Red, Merck, MICA, TITANIUM DIOXIDE, CARMINE
Colorona Blackstar Green, Merck, MICA, CI 77499 (IRON OXIDES)
Colorona Bordeaux, Merck, MICA, CI 77491 (IRON OXIDES)
Colorona Bronze, Merck, MICA, CI 77491 (IRON OXIDES)
Colorona Bronze Fine, Merck, MICA, CI 77491 (IRON OXIDES)
Colorona Fine Gold MP 20, Merck, MICA, CI 77891 (TITANIUM DIOXIDE), CI 77491 (IRON OXIDES)
Colorona Sienna Fine, Merck, MICA, CI 77491 (IRON OXIDES), MICA
Colorona Sienna, Merck, MICA, CI 77491 (IRON OXIDES)
Colorona Precious Gold, Merck, Mica, CI 77891 (Titanium dioxide), Silica, CI 77491 (IRON OXIDES), Tin oxide
Colorona Sun Gold Sparkle MP 29, Merck, MICA, TITANIUM DIOXIDE, IRON OXIDES, MICA, CI 77891, CI 77491 (EU)
Colorona Mica Black, Merck, CI 77499 (Iron oxides), Mica, CI 77891 (Titanium dioxide)
Colorona Bright Gold, Merck, Mica, CI 77891 (Titanium dioxide), CI 77491 (Iron oxides)
Colorona Blackstar Gold, Merck, MICA, CI 77499 (IRON OXIDES)
Colorona® SynCopper, Merck, Synthetic Fluorphlogopite (and) Iron Oxides
Colorona® SynBronze, Merck, Synthetic Fluorphlogopite (and) Iron Oxides Additional particularly preferred pigments with the trade name Xirona® are, for example:

Xirona® Golden Sky, Merck, Silica, CI 77891 (Titanium Dioxide), Tin Oxide
Xirona® Caribbean Blue, Merck, Mica, CI 77891 (Titanium Dioxide), Silica, Tin Oxide
Xirona® Kiwi Rose, Merck, Silica, CI 77891 (Titanium Dioxide), Tin Oxide
Xirona® Magic Mauve, Merck, Silica, CI 77891 (Titanium Dioxide), Tin Oxide
Xirona® Le Rouge, Merck, Iron Oxides (and) Silica In addition, particularly preferred pigments with the trade name Unipure® are, for example:

Unipure Red LC 381 EM, Sensient CI 77491 (Iron Oxides), Silica
Unipure Black LC 989 EM, Sensient, CI 77499 (Iron Oxides), Silica
Unipure Yellow LC 182 EM, Sensient, CI 77492 (Iron Oxides), Silica Likewise particularly preferred pigments with the trade name Flamenco® are, for example:

Flamenco® Summit Turquoise T30D, BASF, Titanium Dioxide (and) Mica
Flamenco® Super Violet 530Z, BASF, Mica (and) Titanium Dioxide In the context of another embodiment, agent (a) and/or agent (b) used in the method can also contain one or more dyeing compounds from the group of organic pigments.

Organic pigments are correspondingly insoluble organic dyes or color lakes which may be selected, for example, from the group of nitroso, nitro, azo, xanthene, anthraquinone, isoindolinone, isoindoline, quinacridone, perinone, perylene, diketopyrrolopyorrole, indigo, thioindido, dioxazine, and/or triarylmethane compounds.

Particularly well suited organic pigments can for example include carmine, quinacridone, phthalocyanine, sorghum, blue pigments with the Color Index numbers CI 42090, CI 69800, CI 69825, CI 73000, CI 74100 or CI 74160, yellow pigments with the Color Index numbers CI 11680, CI 11710, CI 15985, CI 19140, CI 20040, CI 21100, CI 21108, CI 47000 or CI 47005, green pigments with the Color Index numbers CI 61565, CI 61570 or CI 74260, orange pigments with the Color Index numbers CI 11725, CI 15510, CI 45370 or CI 71105, and red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, the method is characterized in that agent (a) and/or agent (b) contains at least one dyeing compound from the group of organic pigments, selected from the group consisting of carmine, quinacridone, phthalocyanine, sorghum, blue pigments with the Color Index numbers CI 42090, CI 69800, CI 69825, CI 73000, CI 74100 or CI 74160, yellow pigments with the Color Index numbers CI 11680, CI 11710, CI 15985, CI 19140, CI 20040, CI 21100, CI 21108, CI 47000 or CI 47005, green pigments with the Color Index numbers CI 61565, CI 61570 or CI 74260, orange pigments with the Color Index numbers CI 11725, CI 15510, CI 45370 or CI 71105, and red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 or CI 75470, and mixtures thereof.

The organic pigment can also be a color lake. The term color lake within the meaning of the invention is understood to mean particles which comprise a layer of absorbed dyes, with the unit consisting of particles and dye being insoluble under the above-mentioned conditions. The particles may be, for example, inorganic substrates which may be aluminum, silica, calcium borosilicate, calcium aluminum borosilicate or aluminum.

For example, the alizarin color lake can be used as the color lake.

In the context of another embodiment of the method, agent (a) and/or agent (b) can also contain one or more dyeing compounds from the group of organic pigments.

In another particularly preferred embodiment, a method is characterized in that agent (a) and/or agent (b) contains at least one dyeing compound from the group of organic pigments, selected from the group of carmine, quinacridone, phthalocyanine, sorghum, blue pigments with the Color Index numbers CI 42090, CI 69800, CI 69825, CI 73000, CI 74100 or CI 74160, yellow pigments with the Color Index numbers CI 11680, CI 11710, CI 15985, CI 19140, CI 20040, CI 21100, CI 21108, CI 47000 or CI 47005, green pigments with the Color Index numbers CI 61565, CI 61570 or CI 74260, orange pigments with the Color Index numbers CI 11725, CI 15510, CI 45370 or CI 71105, and red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

Likewise suitable dyeing compounds from the group of the pigments are inorganic and/or organic pigments which have been modified with a polymer. Polymer modification makes it possible, for example, to increase the affinity of the pigments for the respective material of the at least one layer.

In agent (a) and/or agent (b), what are referred to as metal effect pigments can also be used as the dyeing compound.

The metal effect pigments may in particular contain pigments based on a lamellar substrate platelet, pigments based on lenticular substrate platelets and/or pigments based on substrate platelets which comprise vacuum metalized pigments (VMP). In these metal effect pigments, the substrate platelets comprise a metal, preferably aluminum, or an alloy. Metal effect pigments based on metal substrate platelets preferably have a coating which, inter alia, acts as a protective layer.

Suitable metal effect pigments comprise, for example, the pigments Alegrace® Marvelous, Alegrace© Gorgeous or Alegrace® Aurous from Schlenk Metallic Pigments.

Likewise suitable metal effect pigments are the aluminum-based pigments of the SILVERDREAM series and also the pigments based on aluminum or on copper/zinc-containing metal alloys, of the VISIONAIRE series from Eckart.

Owing to their excellent light and temperature resistance, the use of the aforementioned pigments in agent (a) and/or (b) is very particularly preferred. It is furthermore preferred if the pigments used have a specific particle size. This particle size on the one hand leads to a uniform distribution of the pigments in the polymer film formed and, on the other hand, avoids a rough hair or skin feel after the application of the cosmetic agent. It is therefore advantageous according to the invention if the at least one pigment has an average particle size $D_{50}$ from 1 to 50 μm, preferably from 5 to 45 μm, preferably from 10 to 40 μm, in particular from 14 to 30 μm. The average particle size $D_{50}$ can be determined, for example, using dynamic light scattering (DLS).

In a further preferred embodiment, the method is characterized in that agent (a) further contains one or more dyeing compound(s) in the form of pigments in a total amount of 0.01 to 10 wt %, preferably 0.1 to 8 wt %, more preferably 0.2 to 6 wt %, and most particularly preferably 0.5 to 4.5 wt %, relative to the total weight of agent (a).

In a further likewise preferred embodiment, the method is characterized in that agent (b) further contains one or more dyeing compound(s) in the form of pigments in a total amount of 0.01 to 10 wt %, preferably 0.1 to 8 wt %, more preferably 0.2 to 6 wt %, and most particularly preferably 0.5 to 4.5 wt %, relative to the total weight of agent (b).

The agents (a) and/or agents (b) used in the method can also contain one or more direct dyes as dyeing compound(s). Direct dyes are dyes which attach directly to the hair and require no oxidative process to form a color. Direct dyes are usually nitrophenylenediamines, nitroaminophenols, azo dyes, anthraquinones, triarylmethane dyes, or indophenols.

Within the meaning of the present invention, the direct dyes have a solubility in water (760 mmHg) at 25° C. of more than 0.5 g/l and are therefore not to be regarded as pigments.

Within the meaning of the present invention, the direct dyes preferably have a solubility in water (760 mmHg) at 25° C. of more than 1 g/L.

Direct dyes can be divided into anionic, cationic, and non-ionic direct dyes.

In a further preferred embodiment, the method is characterized in that agent (a) and/or agent (b) further contains, as dyeing compound, at least one anionic, cationic and/or nonionic direct dye.

In a further preferred embodiment, the method is characterized in that agent (a) and/or agent (b) further contains at least one dyeing compound from the group of anionic, nonionic and/or cationic direct dyes.

Suitable cationic direct dyes are for example Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51, Basic Red 76

Nonionic nitro dyes and quinone dyes and neutral azo dyes can for example be used as nonionic direct dyes. Suitable nonionic direct dyes are the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis (2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl) amino-4-nitrobenzene, 2-[(4-amino-2-nitrophenyl)amino] benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

In the course of the work leading to this invention, it was found that colorings having a particularly high color intensity can be produced in particular with agents (a) and/or (b) which contain at least one anionic direct dye.

In an explicitly very particularly preferred embodiment, the method is therefore characterized in that agent (a) and/or agent (b) further contains at least one anionic direct dye as dyeing compound.

Anionic direct dyes are also referred to as acid dyes. Acid dyes mean direct dyes that have at least one carboxylic acid group (—COOH) and/or a sulfonic acid group (—SO$_3$H). Depending on the pH, the protonated forms (—COOH, —SO$_3$H) of the carboxylic acid or sulfonic acid groups are present in equilibrium with their deprotonated forms (—COO$^-$, —SO$_3^-$). The proportion of the protonated forms increases with a decreasing pH. If direct dyes are used in the form of their salts, the carboxylic acid groups or sulfonic acid groups are present in the deprotonated form and are neutralized with corresponding stoichiometric equivalents of cations in order to maintain electroneutrality. The acid dyes can also be used in the form of the sodium salts thereof and/or the potassium salts thereof.

Within the meaning of the present invention, the acid dyes have a solubility in water (760 mmHg) at 25° C. of more than 0.5 g/l and are therefore not to be regarded as pigments. Within the meaning of the present invention, the acid dyes preferably have a solubility in water (760 mmHg) at 25° C. of more than 1 g/L.

The alkaline earth metal salts (for example calcium salts and magnesium salts) or aluminum salts of acid dyes often have poorer solubility than the corresponding alkali metal salts. When the solubility of these salts is below 0.5 g/L (25° C., 760 mmHg), they do not fall under the definition of a direct dye.

An essential feature of the acid dyes is their ability to form anionic charges, with the carboxylic acid groups or sulfonic acid groups responsible for this usually being linked to various chromophore systems. Suitable chromophore systems are found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

In the context of one embodiment, therefore, preference is given to a method for dyeing keratinous material which is characterized in that agent (a) and/or agent (b) further contains, as dyeing compound, at least one anionic direct dye selected from the group of nitrophenylendiamines, nitroaminophenols, azo dyes, anthraquinone dyes, triarylmethane dyes, xanthene dyes, rhodamine dyes, oxazine dyes and/or indophenol dyes, with the dyes in the aforementioned group each having at least one carboxylic acid group (—COOH), a sodium carboxylate group (—COONa), a potassium carboxylate group (—COOK), a sulfonic acid group (—SO$_3$H), a sodium sulfonate group (—SO$_3$Na) and/or a potassium sulfonate group (—SO$_3$K).

For example, as particularly well-suited acid dyes, one or more compounds can be selected from the following group: Acid Yellow 1 (D&C Yellow 7, Citronin A, Ext. D&C Yellow No. 7, Japan Yellow 403, CI 10316, COLIPA no B001), Acid Yellow 3 (COLIPA no: C 54, D&C Yellow No 10, Quinoline Yellow, E104, Food Yellow 13), Acid Yellow 9 (CI 13015), Acid Yellow 17 (CI 18965), Acid Yellow 23 (COLIPA no C. 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA no C015), Acid Orange 10 (CI 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; ACID ORANGE 24; Japan Brown 201; D & C Brown No. 1), Acid Red 14 (C.I. 14720), Acid Red 18 (E124, Red 18; CI 16255), Acid Red 27 (E 123, CI 16185, C-Rot 46, Echtrot D, FD&C Red Nr. 2, Food Red 9, Naphtholrot S), Acid Red 33 (Red 33, Fuchsia Red, D&C Red 33, CI 17200), Acid Red 35 (CI C.I. 18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red no 106 Pontacyl Brilliant Pink), Acid Red 73 (CI CI 27290), Acid Red 87 (Eosin, CI 45380), Acid Red 92 (COLIPA no C53, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet no 2, C.I. 60730, COLIPA no C063), Acid Violet 49 (CI 42640), Acid Violet 50 (CI 50325), Acid Blue 1 (Patent Blue, CI 42045), Acid Blue 3 (Patent Blau V, CI 42051), Acid Blue 7 (CI 42080), Acid Blue 104 (CI 42735), Acid Blue 9 (E 133, Patentblau AE, Amidoblau AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I. 42100), Acid Green 22 (C.I. 42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black no 401, Naphthalene Black 10B, Amido Black 10B, CI 20 470, COLIPA no B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The water solubility of the anionic direct dyes can be determined, for example, in the following way. 0.1 g of the anionic direct dye is added to a beaker. A stirrer bar is added. 100 ml of water are then added. This mixture is heated to 25° C. on a magnetic stirrer, with stirring. Stirring is carried out for 60 minutes. Thereafter, the aqueous mixture is visually assessed. If undissolved residues remain, the amount of water is increased, for example in steps of 10 ml. Water is added until the amount of dye used has completely dissolved. If the dye-water mixture cannot be visually assessed due to the high intensity of the dye, the mixture is filtered. If a proportion of undissolved dye remains on the filter paper, the solubility experiment is repeated with a greater amount of water. If 0.1 g of the anionic direct dye dissolves in 100 ml of water at 25° C., the solubility of the dye is 1 g/L.

Acid Yellow 1 has the name 8-hydroxy-5,7-dinitro-2-naphthalenesulfonic acid, disodium salt, and has a solubility in water of at least 40 g/L (25° C.).

Acid Yellow 3 is a mixture of the sodium salts of mono- and disulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid and the water solubility thereof is greater than 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is readily soluble in water at 25° C.

Acid Orange 7 is the sodium salt of 4-[(2-hydroxy-1-naphthyl)azo]benzenesulfonate. The water solubility thereof is more than 7 g/L (25° C.).

Acid Red 18 is the trisodium salt of 7-hydroxy-8-[(E)-(4-sulfonato-1-naphthyl)-diazenyl)]-1,3-naphthalenedisulfonate and has a very high water solubility of more than 20 wt %.

Acid Red 33 is the disodium salt of 5-amino-4-hydroxy-3-(phenylazo)-naphthalene-2,7-disulfonate, and the water solubility thereof is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, the water solubility of which is stated as being greater than 10 g/L (25° C.).

Acid Blue 9 is the disodium salt of 2-({4-[N-ethyl(3-sulfonatobenzyl]amino]phenyl}{4-[(N-ethyl(3-sulfonatobenzyl)imino]-2,5-cyclohexadien-1-ylidene}methy)-benzenesulfonate and has a water solubility of more than 20 wt % (25° C.).

A very particularly preferred method is therefore characterized in that agent (a) and/or agent (b) further contains at least one dyeing compound from the group of anionic direct dyes, selected from the group of Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The direct dye(s), in particular the anionic direct dyes, can be used in different amounts in agent (a) and/or agent (b) depending on the desired color intensity. It was possible to obtain particularly good results if agent (a) and/or agent (b) further contains one or more direct dyes as dyeing compound in a total amount of 0.01 to 10 wt %, preferably 0.1 to 8 wt %, more preferably 0.2 to 6 wt %, and most particularly preferably 0.5 to 4.5 wt %, in each case relative to the total weight of said agent.

In a further preferred embodiment, the method is characterized in that agent (a) and/or agent (b) further contains one or more direct dyes as dyeing compound in a total amount of 0.01 to 10 wt %, preferably 0.1 to 8 wt %, more preferably 0.2 to 6 wt %, and most particularly preferably 0.5 to 4.5 wt %, relative to the total weight of agent (a) and/or of agent (b).

Preferred embodiments of the method with respect to the dyeing compounds are disclosed below:

1. A method for dyeing keratinous material, in particular human hair, comprising the following steps:
    applying an agent (v) to the keratinous material, wherein agent (v) contains:
    (v1) hydrogen peroxide,
    applying an agent (a) to the keratinous material, wherein agent (a) contains:
    (a1) at least one organosilicon compound from the group of silanes having one, two or three silicon atoms,
    (a2) at least one dyeing compound comprising at least one inorganic pigment selected from the group of colored metal oxides, metal hydroxides, metal oxide hydrates, silicates, metal sulfides, complex metal cyanides, metal sulfates, bronze pigments and mixtures thereof,
    applying an agent (b) to the keratinous material, wherein agent (b) contains:
    (b1) at least one sealing reagent.

2. A method for dyeing keratinous material, in particular human hair, comprising the following steps:
    applying an agent (v) to the keratinous material, wherein agent (v) contains:
    (v1) hydrogen peroxide,
    applying an agent (a) to the keratinous material, wherein agent (a) contains:
    (a1) at least one organosilicon compound from the group of silanes having one, two or three silicon atoms, and
    (a2) at least one dyeing compound comprising at least one inorganic pigment selected from the group of colored metal oxides, metal hydroxides, metal oxide hydrates, silicates, metal sulfides, complex metal cyanides, metal sulfates, bronze pigments and mixtures thereof and at least one pigment selected from the group consisting of pigments based on a lamellar metallic substrate platelet, pigments based on a lenticular metallic substrate platelet, pigments based on a metallic substrate platelet comprising a "vacuum metallized pigment" (VMP) and mixtures thereof,
    applying an agent (b) to the keratinous material, wherein agent (b) contains:
    (b1) at least one sealing reagent.

3. A method for dyeing keratinous material, in particular human hair, comprising the following steps:
    applying an agent (v) to the keratinous material, wherein agent (v) contains:
    (v1) hydrogen peroxide,
    applying an agent (a) to the keratinous material, wherein agent (a) contains:
    (a1) at least one organosilicon compound from the group of silanes having one, two or three silicon atoms, and
    (a2) at least one dyeing compound comprising at least one inorganic pigment selected from the group of colored metal oxides, metal hydroxides, metal oxide hydrates, silicates, metal sulfides, complex metal cyanides, metal sulfates, bronze pigments and mixtures thereof, and at least one pigment comprising α) a substrate platelet comprising mica, and β) a coating comprising at least one first metal oxide (hydrate) layer comprising $TiO_2$, $SnO_2$ and/or iron oxide(s),
    applying an agent (b) to the keratinous material, wherein agent (b) contains:
    (b1) at least one sealing reagent.

4. A method for dyeing keratinous material, in particular human hair, comprising the following steps:
    applying an agent (v) to the keratinous material, wherein agent (v) contains:
    (v1) hydrogen peroxide,
    applying an agent (a) to the keratinous material, wherein agent (a) contains:
    (a1) at least one organosilicon compound from the group of silanes having one, two or three silicon atoms, and
    (a2) at least one dyeing compound comprising at least one inorganic pigment selected from the group of colored metal oxides, metal hydroxides, metal oxide hydrates, silicates, metal sulfides, complex metal cyanides, metal sulfates, bronze pigments and mixtures thereof,
    applying an agent (b) to the keratinous material, wherein agent (b) contains:
    (b1) at least one sealing reagent comprising a film-forming polymer, and
    (b2) at least one dyeing compound comprising at least one pigment selected from the group consisting of pigments based on a lamellar metallic substrate platelet, pigments based on a lenticular metallic substrate platelet, pigments based on a metallic substrate platelet comprising a "vacuum metallized pigment" (VMP) and mixtures thereof.

5. A method for dyeing keratinous material, in particular human hair, comprising the following steps:

applying an agent (v) to the keratinous material, wherein agent (v) contains:

(v1) hydrogen peroxide, applying an agent (a) to the keratinous material, wherein agent (a) contains:

(a1) at least one organosilicon compound from the group of silanes having one, two or three silicon atoms, and (a2) at least one dyeing compound comprising at least one inorganic pigment selected from the group of colored metal oxides, metal hydroxides, metal oxide hydrates, silicates, metal sulfides, complex metal cyanides, metal sulfates, bronze pigments and mixtures thereof, applying an agent (b) to the keratinous material, wherein agent (b) contains:

(b1) at least one sealing reagent comprising a film-forming polymer, and (b2) at least one dyeing compound comprising a pigment comprising α) a substrate platelet comprising mica, and β) a coating comprising at least one first metal oxide (hydrate) layer comprising $TiO_2$, $SnO_2$ and/or iron oxide(s).

6. A method for dyeing keratinous material, in particular human hair, comprising the following steps:

applying an agent (v) to the keratinous material, wherein agent (v) contains:

(v1) hydrogen peroxide, applying an agent (a) to the keratinous material, wherein agent (a) contains:

(a1) at least one organosilicon compound from the group of silanes having one, two or three silicon atoms, and (a2) at least one dyeing compound comprising at least one inorganic pigment selected from the group of colored metal oxides, metal hydroxides, metal oxide hydrates, silicates, metal sulfides, complex metal cyanides, metal sulfates, bronze pigments and mixtures thereof, applying an agent (b) to the keratinous material, wherein agent (b) contains:

(b1) at least one sealing reagent comprising a film-forming polymer, and (b2) at least one dyeing compound comprising a pigment comprising α) a substrate platelet comprising borosilicate glass, and β) a coating comprising at least one first metal oxide (hydrate) layer, comprising $TiO_2$, $SnO_2$, $SiO_2$ and/or iron oxide(s).

7. A method for dyeing keratinous material, in particular human hair, comprising the following steps:

applying an agent (v) to the keratinous material, wherein agent (v) contains:

(v1) hydrogen peroxide, applying an agent (a) to the keratinous material, wherein agent (a) contains:

(a1) at least one organosilicon compound from the group of silanes having one, two or three silicon atoms, and (a2) at least one dyeing compound comprising at least one organic pigment which is selected from the group consisting of carmine, quinacridone, phthalocyanine, sorghum, blue pigments having the Color Index Numbers CI 42090, CI 69800, CI 69825, CI 73000, CI 74100, CI 74160, yellow pigments having the Color Index Numbers CI 11680, CI 11710, CI 15985, CI 19140, CI 20040, CI 21100, CI 21108, CI 47000, CI 47005, green pigments having the Color Index Numbers CI 61565, CI 61570, CI 74260, orange pigments having the Color Index Numbers CI 11725, CI 15510, CI 45370, CI 71105, red pigments having the Color Index Numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof, applying an agent (b) to the keratinous material, wherein agent (b) contains:

(b1) at least one sealing reagent.

8. A method for dyeing keratinous material, in particular human hair, comprising the following steps:

applying an agent (v) to the keratinous material, wherein agent (v) contains:

(v1) hydrogen peroxide, applying an agent (a) to the keratinous material, wherein agent (a) contains:

(a1) at least one organosilicon compound from the group of silanes having one, two or three silicon atoms, and (a2) at least one dyeing compound comprising at least one organic pigment which is selected from the group consisting of carmine, quinacridone, phthalocyanine, sorghum, blue pigments having the Color Index Numbers CI 42090, CI 69800, CI 69825, CI 73000, CI 74100, CI 74160, yellow pigments having the Color Index Numbers CI 11680, CI 11710, CI 15985, CI 19140, CI 20040, CI 21100, CI 21108, CI 47000, CI 47005, green pigments having the Color Index Numbers CI 61565, CI 61570, CI 74260, orange pigments having the Color Index Numbers CI 11725, CI 15510, CI 45370, CI 71105, red pigments having the Color Index Numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof, and at least one pigment selected from the group consisting of pigments based on a lamellar, metallic substrate platelet, pigments based on a lenticular, metallic substrate platelet which comprises vacuum metallized pigments (VMP), and mixtures thereof, applying an agent (b) to the keratinous material, wherein agent (b) contains:

(b1) at least one sealing reagent.

9. A method for dyeing keratinous material, in particular human hair, comprising the following steps:

applying an agent (v) to the keratinous material, wherein agent (v) contains:

(v1) hydrogen peroxide, applying an agent (a) to the keratinous material, wherein agent (a) contains:

(a1) at least one organosilicon compound from the group of silanes having one, two or three silicon atoms, and (a2) at least one dyeing compound comprising at least one organic pigment which is selected from the group consisting of carmine, quinacridone, phthalocyanine, sorghum, blue pigments having the Color Index Numbers CI 42090, CI 69800, CI 69825, CI 73000, CI 74100, CI 74160, yellow pigments having the Color Index Numbers CI 11680, CI 11710, CI 15985, CI 19140, CI 20040, CI 21100, CI 21108, CI 47000, CI 47005, green pigments having the Color Index Numbers CI 61565, CI 61570, CI 74260, orange pigments having the Color Index Numbers CI 11725, CI 15510, CI 45370, CI 71105, red pigments having the Color Index Numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof, and at least one pigment comprising α) a substrate platelet comprising mica, and β) a coating comprising at least one first metal oxide (hydrate) layer comprising TiO$_2$, SnO$_2$ and/or iron oxide(s), applying an agent (b) to the keratinous material, wherein agent (b) contains:

(b1) at least one sealing reagent.

10. A method for dyeing keratinous material, in particular human hair, comprising the following steps:

applying an agent (v) to the keratinous material, wherein agent (v) contains:

(v1) hydrogen peroxide, applying an agent (a) to the keratinous material, wherein agent (a) contains:

(a1) at least one organosilicon compound from the group of silanes having one, two or three silicon atoms, and (a2) at least one dyeing compound comprising at least one organic pigment which is selected from the group consisting of carmine, quinacridone, phthalocyanine, sorghum, blue pigments having the Color Index Numbers CI 42090, CI 69800, CI 69825, CI 73000, CI 74100, CI 74160, yellow pigments having the Color Index Numbers CI 11680, CI 11710, CI 15985, CI 19140, CI 20040, CI 21100, CI 21108, CI 47000, CI 47005, green pigments having the Color Index Numbers CI 61565, CI 61570, CI 74260, orange pigments having the Color Index Numbers CI 11725, CI 15510, CI 45370, CI 71105, red pigments having the Color Index Numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof, applying an agent (b) to the keratinous material, wherein agent (b) contains:

(b1) at least one sealing reagent comprising a film-forming polymer, and (b2) at least one dyeing compound comprising at least one pigment selected from the group consisting of pigments based on a lamellar metallic substrate platelet, pigments based on a lenticular metallic substrate platelet, pigments based on a metallic substrate platelet comprising a "vacuum metallized pigment" (VMP) and mixtures thereof.

11. A method for dyeing keratinous material, in particular human hair, comprising the following steps:

applying an agent (v) to the keratinous material, wherein agent (v) contains:

(v1) hydrogen peroxide, applying an agent (a) to the keratinous material, wherein agent (a) contains:

(a1) at least one organosilicon compound from the group of silanes having one, two or three silicon atoms, and (a2) at least one dyeing compound comprising at least one organic pigment which is selected from the group consisting of carmine, quinacridone, phthalocyanine, sorghum, blue pigments having the Color Index Numbers CI 42090, CI 69800, CI 69825, CI 73000, CI 74100, CI 74160, yellow pigments having the Color Index Numbers CI 11680, CI 11710, CI 15985, CI 19140, CI 20040, CI 21100, CI 21108, CI 47000, CI 47005, green pigments having the Color Index Numbers CI 61565, CI 61570, CI 74260, orange pigments having the Color Index Numbers CI 11725, CI 15510, CI 45370, CI 71105, red pigments having the Color Index Numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof, applying an agent (b) to the keratinous material, wherein agent (b) contains:

(b1) at least one sealing reagent comprising a film-forming polymer, and (b2) at least one dyeing compound comprising a pigment comprising α) a substrate platelet comprising mica, and β) a coating comprising at least one first metal oxide (hydrate) layer comprising TiO$_2$, SnO$_2$ and/or iron oxide(s).

12. A method for dyeing keratinous material, in particular human hair, comprising the following steps:

applying an agent (v) to the keratinous material, wherein agent (v) contains:

(v1) hydrogen peroxide, applying an agent (a) to the keratinous material, wherein agent (a) contains:

(a1) at least one organosilicon compound from the group of silanes having one, two or three silicon atoms, and (a2) at least one dyeing compound comprising at least one organic pigment which is selected from the group consisting of carmine, quinacridone, phthalocyanine, sorghum, blue pigments having the Color Index Numbers CI 42090, CI 69800, CI 69825, CI 73000, CI 74100, CI 74160, yellow pigments having the Color Index Numbers CI 11680, CI 11710, CI 15985, CI 19140, CI 20040, CI 21100, CI 21108, CI 47000, CI 47005, green pigments having the Color Index Numbers CI 61565, CI 61570, CI 74260, orange pigments having the Color Index Numbers CI 11725, CI 15510, CI 45370, CI 71105, red pigments having the Color Index Numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof, applying an agent (b) to the keratinous material, wherein agent (b) contains:

(b1) at least one sealing reagent comprising a film-forming polymer, and (b2) at least one dyeing compound comprising a pigment comprising α) a substrate platelet comprising borosilicate glass, and β) a coating comprising at least one first metal oxide (hydrate) layer, comprising TiO$_2$, SnO$_2$, SiO$_2$ and/or iron oxide(s).

13. A method for dyeing keratinous material, in particular human hair, comprising the following steps:

applying an agent (v) to the keratinous material, wherein agent (v) contains:

(v1) hydrogen peroxide, applying an agent (a) to the keratinous material, wherein agent (a) contains:

(a1) at least one organosilicon compound from the group of silanes having one, two or three silicon atoms, (a2) at least one dyeing compound from the group of pigments and/or direct dyes comprising a pigment from the group of iron oxide pigments, wherein the iron oxide pigment has a particle diameter in the range from 100 to 1000 nm, more preferably 150 nm 700 nm, applying an agent (b) to the keratinous material, wherein agent (b) contains:

(b1) at least one sealing reagent.

14. A method for dyeing keratinous material, in particular human hair, comprising the following steps:
- applying an agent (v) to the keratinous material, wherein agent (v) contains:
- (v1) hydrogen peroxide,
- applying an agent (a) to the keratinous material, wherein agent (a) contains:
- (a1) at least one organosilicon compound from the group of silanes having one, two or three silicon atoms,
- (a2) at least one dyeing compound from the group of pigments and/or direct dyes comprising a pigment from the group of iron oxide pigments, wherein the iron oxide pigment has a particle diameter in the range from 100 to 1000 nm, more preferably 150 nm 700 nm, and at least one pigment selected from the group consisting of pigments based on a lamellar metallic substrate platelet, pigments based on a lenticular metallic substrate platelet, pigments based on a metallic substrate platelet comprising a "vacuum metallized pigment" (VMP) and mixtures thereof,
- applying an agent (b) to the keratinous material, wherein agent (b) contains:
- (b1) at least one sealing reagent.

15. A method for dyeing keratinous material, in particular human hair, comprising the following steps:
- applying an agent (v) to the keratinous material, wherein agent (v) contains:
- (v1) hydrogen peroxide,
- applying an agent (a) to the keratinous material, wherein agent (a) contains:
- (a1) at least one organosilicon compound from the group of silanes having one, two or three silicon atoms,
- (a2) at least one dyeing compound from the group of pigments and/or direct dyes comprising a pigment from the group of iron oxide pigments, wherein the iron oxide pigment has a particle diameter in the range from 100 to 1000 nm, more preferably 150 nm 700 nm,
- applying an agent (b) to the keratinous material, wherein agent (b) contains:
- (b1) at least one sealing reagent comprising a film-forming polymer, and
- (b2) at least one dyeing compound from the group of pigments and/or direct dyes comprising at least one pigment selected from the group consisting of pigments based on a lamellar metallic substrate platelet, pigments based on a lenticular metallic substrate platelet, pigments based on a metallic substrate platelet comprising a "vacuum metallized pigment" (VMP) and mixtures thereof.

The agent can also contain one or more surfactants. The term surfactants is understood to mean surface-active substances. A distinction is made between anionic surfactants consisting of a hydrophobic functional group and a negatively charged hydrophilic head group, amphoteric surfactants which bear both a negative and a compensating positive charge, cationic surfactants which have a positively charged hydrophilic group in addition to a hydrophobic functional group, and non-ionic surfactants which have no charges but strong dipole moments and are strongly hydrated in aqueous solution.

"Zwitterionic surfactants" refers to surface-active compounds that bear at least one quaternary ammonium group and at least one —COO(-) or —SO3(-) group in the molecule. Particularly suitable zwitterionic surfactants are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethylcarboxymethyl glycinate. A preferred zwitterionic surfactant is the fatty acid amide derivative known under the INCI name Cocamidopropyl Betaine.

Ampholytic surfactants are understood to include surface-active compounds that contain at least one free amino group and at least one —COOH or —SO$_3$H group in addition to a $C_8$-$C_{24}$ alkyl group or acyl group in the molecule and are capable of forming inner salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 24 carbon atoms in the alkyl group. Typical examples of amphoteric or zwitterionic surfactants are alkyl betaines, alkylamidobetaines, amino propionate, aminoglycinates, imidazolinium betaines and sulfobetaines.

Particularly preferred ampholytic surfactants are N-cocoalkyl aminopropionate, cocoacylaminoethyl aminopropionate, and $C_{12}$-$C_{18}$ acyl sarcosine.

The agents can also contain at least one non-ionic surfactant. Suitable non-ionic surfactants are alkyl polyglycosides and alkylene oxide adducts to fatty alcohols and fatty acids with in each case 2 to 30 mol of ethylene oxide per mole of fatty alcohol or fatty acid. Preparations with good properties are likewise obtained when they contain fatty acid esters of ethoxylated glycerin as non-ionic surfactants which have been reacted with at least 2 mol ethylene oxide.

Furthermore, the agents can additionally also contain at least one cationic surfactant. Cationic surfactants are understood to mean surfactants, i.e. surface-active compounds, each having one or more positive charges.

Cationic surfactants contain exclusively positive charges. Typically, these surfactants are composed of a hydrophobic part and a hydrophilic head group, with the hydrophobic part generally consisting of a hydrocarbon framework (e. g., consisting of one or two linear or branched alkyl chains), and the positive charge(s) being located in the hydrophilic head group. Examples of cationic surfactants are:
- quaternary ammonium compounds which, as hydrophobic functional groups, can bear one or two alkyl chains having a chain length of 8 to 28 C atoms,
- quaternary phosphonium salts substituted with one or more alkyl chains having a chain length of 8 to 28 C atoms, or
- tertiary sulfonium salts.

Furthermore, the cationic charge can also be part of a heterocyclic ring (for example an imidazolium ring or a pyridinium ring) in the form of an onium structure. In addition to the functional unit carrying the cationic charge, the cationic surfactant can also contain further uncharged functional groups, as is the case, for example, with esterquats. The cationic surfactants are used in a total amount from 0.1 to 45 wt. %, preferably 1 to 30 wt. %, and very particularly preferably from 1 to 15 wt. %, based on the total weight of each agent.

Furthermore, the agents can also contain at least one anionic surfactant. Anionic surfactants are surface-active agents with exclusively anionic charges (neutralized by a corresponding counter cation). Examples of anionic surfactants are fatty acids, alkyl sulfates, alkyl ether sulfates, and ether carboxylic acids having 12 to 20 C atoms in the alkyl group and up to 16 glycol ether groups in the molecule.

The anionic surfactants are used in a total amount from 0.1 to 45 wt. %, preferably 1 to 30 wt. %, and very particularly preferably from 1 to 15 wt. %, based on the total weight of each agent.

Agent (a) and/or agent (b) may further contain a matting agent. Suitable matting agents include, for example, (modified) starches, waxes, talc and/or (modified) silicas. The amount of matting agents is preferably between 0.1 and 10 wt. % based on the total amount of agent (a) or agent (b). Preferably, agent (a) comprises a matting agent.

Agent (a) and/or agent (b) can also contain a thickener.

If agents (a) and/or (b) are used, they must not be too thin and must not drip down from the keratinous material. For this reason, it may be preferred for agent (a) and/or (b) to further contain a thickener.

In the context of one embodiment, preference is thus given to a method for dyeing keratinous material, characterized in that agent (a) and/or agent (b) further contains a thickener.

The agents can also contain other active ingredients, auxiliaries and additives, for example solvents, fatty components, for example $C_8$-$C_{30}$ fatty acid triglycerides, $C_8$-$C_{30}$ fatty acid monoglycerides, $C_8$-$C_{30}$ fatty acid diglycerides and/or hydrocarbons; structurants such as glucose, maleic acid and lactic acid, hair-conditioning compounds such as phospholipids, for example lecithin and cephalins; perfume oils, dimethyl isosorbide and cyclodextrins; fiber structure-improving agents, in particular mono-, di- and oligosaccharides, for example glucose, galactose, fructose and lactose; dyes for coloring the product; anti-dandruff active ingredients such as piroctone olamine, zinc omadine and climbazole; amino acids and oligopeptides; animal and/or vegetable-based protein hydrolyzates, as well as in the form of their fatty acid condensation products or optionally anionically or cationically modified derivatives; plant-based oils, light stabilizers and UV blockers; active ingredients such as panthenol, pantothenic acid, pantolactone, allantoin, pyrrolidinone carboxylic acids and the salts thereof, and bisabolol; polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; swelling agents and penetrants such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3-distearate; and propellants such as propane-butane mixtures, $N_2O$, dimethyl ether, $CO_2$ and air.

The selection of these additional substances is made by the skilled artisan according to the desired properties of the agents. In regard to other facultative components and the employed amounts of said components, reference is made expressly to relevant handbooks known to the skilled artisan. The additional active ingredients and auxiliaries are used in the preparations according the invention preferably in each case in amounts from 0.0001 to 25 wt. %, in particular from 0.0005 to 15 wt. %, based on the total weight of the particular agent.

Method for Dyeing Keratinous Materials

In the context of the method according to the invention, agents (v), (a) and (b) are applied to the keratinous material, in particular to human hair. The agents (v), (a) and (b) are thus ready-to-use agents. The agents (v), (a) and (b) are different to each other.

The agents (a) and (b) can in principle be applied simultaneously or consecutively, with preference being given to consecutive application. The agent (v) is applied before agents (a) and (b).

The best results were obtained if agent (v) was first applied to the keratinous materials in a first step, agent (a) was added to the keratinous materials in a second step and agent (b) was applied in a third step.

Very particular preference is therefore given to a method for treating keratinous material, in particular for dyeing keratinous material, in particular human hair, comprising the following steps in the indicated order:
1. in a first step, applying an agent (v) to the keratinous material, wherein agent (v) contains:
   (a1) hydrogen peroxide,
2. in a second step, applying an agent (a) to the keratinous material, wherein agent (a) contains:
   (a1) at least one organosilicon compound from the group of silanes having one, two or three silicon atoms, and
3. in a third step, applying an agent (b) to the keratinous material, wherein agent (b) contains:
   (b1) at least one sealing reagent,
   wherein at least one of agents (a) and (b) additionally contains at least one dyeing compound from the group consisting of pigments and/or direct dyes.

In order to impart a high washout resistance to the dyed keratinous material over a longer period, agents (v), (a) and (b) are also particularly preferably used within one and the same dyeing method, which means that a period of at most a few hours is present between the application of agents (v) and (b).

In the context of a further particularly preferred embodiment, the method is characterized in that agent (v) is applied first, then agent (a) is applied, and agent (b) is applied thereafter, the period between the application of agents (v) and (b) being at most 24 hours, preferably at most 12 hours, and particularly preferably at most 6 hours.

A characterizing feature of the agent (a) is its content of at least one reactive organosilicon compound (a1). The reactive organosilicon compound(s) (a1) participate in an oligomerization or polymerization reaction and, in this way, functionalize the hair surface as soon as they come into contact with it. In the second step of the method, a second agent (b) is applied to the hair. During the application of agent (b), comprising at least one film-forming polymer as sealing reagent (b1), it interacts with the silane film and is thus bound to the keratinous materials. During the application of the agent (b), comprising at least one alkalizing agent or acidifying agent as a sealing reagent (b1), the formation of the silane film is positively influenced. The desired coloring of the keratinous material is carried out by means of the dyeing compound in agent (a) and/or in agent (b). The coloring can be obtained by a colored silane film (the dyeing compound is only in agent (a)), by a colored polymer film (the dyeing compound is only in agent (b), which contains a film-forming polymer as sealing reagent (b1)) or by a colored silane film and by a colored polymer film (agents (a) and (b) each contain at least one dyeing compound and agent (b) contains a film-forming polymer as sealing reagent (b1)).

In the context of a further embodiment, most particular preference is given to a method comprising the following steps in the indicated order (1) applying agent (v) to the keratinous material,
(2) allowing agent (v) to act for a period of 1 minute to 60 minutes, preferably 5 minutes to 25 minutes,
(3) optionally rinsing the keratinous material with water,
(4) applying agent (a) to the keratinous material,
(5) allowing agent (a) to act for a period of 10 seconds to 10 minutes, preferably 10 seconds to 5 minutes,
(6) optionally rinsing the keratinous material with water,
(7) applying agent (b) to the keratinous material,
(8) allowing agent (b) to act for a period of 30 seconds to 30 minutes, preferably 30 seconds to 10 minutes,
(9) rinsing the keratinous material with water.

The rinsing out of the keratinous material with water in steps (3), (6) and (9) of the method is understood, according to the invention, to mean that only water is used for the rinsing process, without any further agent, different from the agents (v), (a) and (b), being used.

In a step (1), agent (v) is first applied to the keratinous materials, in particular human hair.

After application, agent (v) is allowed to act on the keratinous materials. In this context, application times of 1 minute to 60 minutes, preferably of 5 minutes to 25 minutes and very particularly preferably of 10 minutes to 20 minutes on the hair have proven to be particularly advantageous.

In the context of a particularly preferred embodiment of the method according to the invention, agent (v) is rinsed out of the keratinous materials before agent (a) is applied to the hair in the subsequent step.

In a step (4), agent (a) is applied to the keratinous materials, in particular human hair.

After application, agent (a) is allowed to act on the keratinous materials. In this context, application times of 10 seconds to 10 minutes, preferably of 20 seconds to 5 minutes and very particularly preferably of 30 seconds to 2 minutes on the hair have proven to be particularly advantageous.

In the context of a preferred embodiment of the method, agent (a) can now be rinsed out of the keratinous materials before agent (b) is applied to the hair in the subsequent step.

Colorings with likewise good wash-fastness were obtained if agent (b) was applied to the keratinous materials, which still had agent (a) applied thereto.

In step (7), agent (b) is now applied to the keratinous materials. After application, agent (b) is then allowed to act on the hair.

Even with a short application time of agent (b), the method makes it possible to create colorings of particularly good intensity and wash-fastness. Application times of 10 seconds to 10 minutes, preferably of 20 seconds to 5 minutes and very particularly preferably of 30 seconds to 3 minutes on the hair have proven to be particularly advantageous.

In step (9), agent (b) (and optionally agent (a), if still present) is rinsed from the keratinous material with water.

In the context of this embodiment, the sequence of steps (1) to (9) is preferably performed within 24 hours.

Agent (a) contains, with the organosilicon compound(s), a class of highly reactive compounds which, when applied, can participate in hydrolysis or oligomerization and/or polymerization. As a result of their high reactivity, these organosilicon compounds form a film on the keratinous material.

To avoid premature oligomerization or polymerization, it is significantly advantageous for the user to only prepare the ready-to-use agent (a) shortly before application.

In the context of a further embodiment, preference is given to a method comprising the following steps in the indicated order (1) applying an agent (a) to the keratinous material, wherein agent (a) contains:
(v1) hydrogen peroxide,
(2) producing an agent (a) by mixing a first agent (a') and a second agent (a"), wherein
the first agent (a') contains at least one organosilicon compound (a1) from the group of silanes having one, two or three silicon atoms, and
the second agent (a") contains water and, optionally, at least one dyeing compound from the group of the pigments and/or the direct dyes (a2),
(3) applying agent (a) to the keratinous material,
(4) allowing agent (a) to act for a period of 10 seconds to 10 minutes, preferably 10 seconds to 5 minutes,
(5) optionally rinsing the keratinous material with water,
(6) applying agent (b) to the keratinous material,
(7) allowing agent (b) to act for a period of 30 seconds to 30 minutes, preferably 30 seconds to 10 minutes,
(8) rinsing the keratinous material with water.

In order to be able to provide a formulation which is as stable as possible, agent (a') itself is preferably produced so as to be low in water or anhydrous.

In a preferred embodiment, a method is characterized in that agent (a') has a water content of 0.001 to 10 wt. %, preferably 0.5 to 9 wt. %, more preferably 1 to 8 wt. %, and very particularly preferably 1.5 to 7 wt. %, relative to the total weight of agent (a').

The agent (a') can further contain a thickener.

In a preferred embodiment, a method is characterized in that agent (am) has a water content of 15 to 99.9 wt. %, preferably 35 to 99 wt %, more preferably 55 to 99 wt. %, even more preferably 65 to 99 wt. %, and very particularly preferably 75 to 99 wt. %, relative to the total weight of agent (a").

Within this embodiment, the ready-to-use agent (a) is now prepared by mixing agents (a') and (a").

For example, the user can first stir or shake agent (a'), containing the organosilicon compound(s) (a1), with the water-containing agent (a"). The user can now apply this mixture of (a') and (a") to the keratinous materials—either directly after they are prepared or after a short reaction time of 10 seconds to 20 minutes. Subsequently, the user can apply the agent (b) as described above.

It can also be preferred if an agent (a'") which contains at least one dyeing compound from the group of pigments and/or direct dyes (a2) is also used in the method.

In the context of a further embodiment, particular preference is given to a method comprising the following steps in the indicated order (1) applying an agent (a) to the keratinous material, wherein agent (a) contains:
(v1) hydrogen peroxide,
(2) allowing agent (v) to act for a period of 1 minute to 60 minutes, preferably 5 minutes to 25 minutes,
(3) optionally rinsing the keratinous material with water,
(4) producing an agent (a) by mixing a first agent (a'), a second agent (a") and a third agent (a'"), wherein
the first agent (a') contains at least one organosilicon compound (a1) from the group of silanes having one, two or three silicon atoms,
the second agent (a") contains water, and
the third agent (a") contains at least one dyeing compound from the group of pigments and/or direct dyes (a2),
(5) applying agent (a) to the keratinous material,
(6) allowing agent (a) to act for a period of 10 seconds to 10 minutes, preferably 10 seconds to 5 minutes, (7) optionally rinsing the keratinous material with water,
(8) applying agent (b) to the keratinous material,
(9) allowing agent (b) to act for a period of 30 seconds to 30 minutes, preferably 30 seconds to 10 minutes,
(10) rinsing the keratinous material with water.

Within this embodiment, the ready-to-use agent (a) is now prepared by mixing agents (a'), (a") and (a'").

For example, the user can first stir or shake the agent (a') containing the organosilicon compound(s) (a1) with the water-containing agent (a") and then with the agent (a'") containing the at least one dyeing compound. The user can now apply this mixture of (a'), (a") and (a'") to the keratinous materials—either directly after they are prepared or after a short reaction time of 10 seconds to 20 minutes. Subsequently, the user can apply the agent (b) as described above.

For example, the user can first stir or shake the agent (a'") containing the at least one dyeing compound with the water-containing agent (a") and then with the agent (a') containing the organosilicon compound(s) (a1). The user can now apply this mixture of (a'), (a") and (a'") to the keratinous materials—either directly after they are prepared or after a short reaction time of 10 seconds to 20 minutes. Subsequently, the user can apply the agent (b) as described above.

The ready-to-use agent (b) can also be prepared only shortly before the application of the agent (b), especially if it contains at least one dyeing compound. In this case, the ready-to-use agent (b) is prepared, for example, by mixing agents (b') and (b").

For example, the user can stir or shake the agent (b') containing the sealing reagent (b1) and the agent (b") containing the at least one dyeing compound. The user can now apply this mixture of (b') and (b") to the keratinous materials—either directly after they are prepared or after a short reaction time of 10 seconds to 20 minutes.

The at least one dyeing compound (a2) and/or (b2) from the group of pigments and direct dyes is preferably used in the form of a pigment suspension comprising the at least one dyeing compound (a2) and/or (b2) and a liquid carrier medium. The carrier medium is preferably non-aqueous. The carrier medium can comprise, for example, a silicone oil. Correspondingly, agents (a) and (b) can (a2) and/or (b2) further comprise the liquid carrier medium in each case in addition to the two respectively mandatory ingredients (a1) and (b1) and the at least one dyeing compound (a2) and/or (b2).

Multi-Component Packaging Unit (Kit-of-Parts)

To increase convenience of use, the user is preferably provided with all the required agents in the form of a multi-component packaging unit (kit-of-parts).

A second subject of the present invention is therefore a multi-component packaging unit (kit of parts) for dyeing keratinous material, comprising, packaged separately from one another
a first container with an agent (v), wherein the agent (v) contains:
(v1) hydrogen peroxide,
a second container having an agent (a'), wherein agent (a') contains:
(a1) at least one organosilicon compound from the group of silanes having one, two or three silicon atoms, and
a third container having an agent (a"), wherein agent (a") contains:
water, and
a fourth container having an agent (b), wherein agent (b) contains:
(b1) at least one sealing reagent,
wherein the constituents (a1) and (b1) have been disclosed in detail above and at least one of agents (a) and (b) additionally contains at least one dyeing compound from the group consisting of pigments and/or direct dyes.

A preferred embodiment comprises a multi-component packaging unit (kit of parts) for dyeing keratinous material, comprising, packaged separately from one another
a first container with an agent (v), wherein the agent (v) contains:
(v1) hydrogen peroxide,
a second container having an agent (a'), wherein agent (a') contains:
(a1) at least one organosilicon compound from the group of silanes having one, two or three silicon atoms, and
a third container having an agent (a"), wherein agent (a") contains:
water, and
a fourth container having an agent (a'"), wherein agent (a'") contains:
(a2) at least one dyeing compound from the group of pigments and/or direct dyes,
a fifth container having an agent (b), wherein agent (b) contains:
(b1) at least one sealing reagent,
wherein the constituents (v1), (a1), (a2) and (b1) have been disclosed in detail above.

Preferred in the context of another embodiment is a multi-component packaging unit (kit of parts) for dyeing keratinous material, comprising, packaged separately from one another
a first container with an agent (v), wherein the agent (v) contains:
(v1) hydrogen peroxide,
a second container having an agent (a'), wherein agent (a') contains:
at least one organosilicon compound (a1) from the group of silanes having one, two or three silicon atoms, and
a third container having an agent (a"), wherein agent (a") contains:
water and
(a2) at least one dyeing compound from the group of pigments and/or direct dyes, and
a fourth container having an agent (b), wherein agent (b) contains:
(b1) at least one sealing reagent,
wherein the constituents (v1), (a1), (a2) and (b1) have been disclosed in detail above.

Preferred in the context of yet another embodiment is a multi-component packaging unit (kit of parts) for dyeing keratinous material, comprising, packaged separately from one another
a first container with an agent (v), wherein the agent (v) contains:
(v1) hydrogen peroxide,
a second container having an agent (a'), wherein agent (a') contains:
at least one organosilicon compound (a1) from the group of silanes having one, two or three silicon atoms, and
a third container having an agent (a"), wherein agent (a") contains:
(a2) at least one dyeing compound from the group of pigments and/or direct dyes, and
a fourth container having an agent (b), wherein agent (b) contains:
(b1) at least one sealing reagent,
wherein the constituents (v1), (a1), (a2) and (b1) have been disclosed in detail above.

Preferred in the context of another embodiment is a multi-component packaging unit (kit of parts) for dyeing keratinous material, comprising, packaged separately from one another
- a first container with an agent (v), wherein the agent (v) contains:
- (v1) hydrogen peroxide,
- a second container having an agent (a'), wherein agent (a') contains:
- at least one organosilicon compound (a1) from the group of silanes having one, two or three silicon atoms, and
- a third container having an agent (a"), wherein agent (a") contains:
- water, and
- a fourth container having an agent (b), wherein agent (b) contains:
- (b1) at least one sealing reagent comprising a film-forming polymer, and also
- (b2) at least one dyeing compound from the group of pigments and/or direct dyes, wherein the constituents (v1), (a1), (b1) and (b2) have been disclosed in detail above.

Preferred in the context of yet another embodiment is a multi-component packaging unit (kit of parts) for dyeing keratinous material, comprising, packaged separately from one another
- a first container with an agent (v), wherein the agent (v) contains:
- (v1) hydrogen peroxide,
- a second container having an agent (a'), wherein agent (a') contains:
- at least one organosilicon compound (a1) from the group of silanes having one, two or three silicon atoms, and
- a third container having an agent (a"), wherein agent (a") contains:
- Water
- a fourth container having an agent (a'''), wherein agent (a''') contains:
- (a2) at least one dyeing compound from the group of pigments and/or direct dyes,
- a fifth container having an agent (b'), wherein agent (b') contains:
- (b1) at least one sealing reagent comprising a film-forming polymer, and
- a sixth container having an agent (b"), wherein agent (b") contains:
- (b2) at least one dyeing compound from the group of pigments and/or direct dyes, wherein the constituents (v1), (a1), (a2), (b1) and (b2) have been disclosed in detail above.

Preferred in the context of yet another embodiment is a multi-component packaging unit (kit of parts) for dyeing keratinous material, comprising, packaged separately from one another
- a first container with an agent (v), wherein the agent (v) contains:
- (v1) hydrogen peroxide,
- a second container having an agent (a'), wherein agent (a') contains:
- at least one organosilicon compound (a1) from the group of silanes having one, two or three silicon atoms, and
- a third container having an agent (a"), wherein agent (a") contains:
- Water
- a fourth container having an agent (b'), wherein agent (b') contains:
- (b1) at least one sealing reagent comprising a film-forming polymer, and
- a fifth container having an agent (b"), wherein agent (b") contains:
- (b2) at least one dyeing compound from the group of pigments and/or direct dyes, wherein the constituents (v1), (a1), (b1) and (b2) have been disclosed in detail above.

Regarding the additional preferred embodiments of the multi-component packaging unit, the statements made regarding the method apply, mutatis mutandis.

Examples

The following formulations were prepared (unless stated otherwise, all figures are in % by weight of active substance)

| Agent (v) | |
|---|---|
|  | Wt % |
| $H_2O_2$ (50% in water) (v1) | 18 |
| Decyl glucoside (INCI) | 10 |
| Water | up to 100 |

| Agent (a') | |
|---|---|
| Agent (a') | Wt % |
| (3-aminopropyl)triethoxysilane (a1) | 24 |
| Methyltriethoxysilane (a1) | 72 |
| Water | up to 100 |

| Agent (a") | |
|---|---|
| Agent (a") | Wt % |
| Water | 100 |

| Agent (a''') | |
|---|---|
| Agent (a''') | Wt % |
| Pigment mixture (CI 12490, CI 74160 and CI 11680) | 1 |
| PEG 12 dimethicone | up to 100 |

The ready-to-use agent (a) was prepared by mixing 5 g of agent (a'), 5 g of agent (a''') and 15 g of agent (a"). The pH of agent (a) was adjusted to 10.5 by adding ammonia or lactic acid.

| Agent (b) | |
|---|---|
| Agent (b) | Wt % |
| Ethylene/Sodium Acrylate Copolymer (b1) (25% strength solution) | 40 |
| Water | up to 100 |

First, the pre-treatment agent (v) was massaged into a hair strand (Kerling, white Euronaturhaar), allowed to work for 10 minutes and then rinsed out with water.

Thereafter, agent (a) was massaged into the respective strands of hair and allowed to work for 1 minute. The strands were then rinsed with water.

Thereafter, agent (b) was applied to the strands of hair, allowed to act for 1 minute and thereafter also rinsed out with water.

The invention claimed is:

1. A method for dyeing keratinous material, the method comprising:
    applying a first agent to the keratinous material, wherein the first agent comprises hydrogen peroxide and water;
    applying a second agent to the keratinous material, wherein the second agent comprises at least one organosilicon compound selected from the group consisting of silanes having one, two, and three silicon atoms; and
    applying a third agent to the keratinous material, wherein the third agent comprises at least one sealing reagent,
    wherein at least one of the second agent or the third agent further comprises at least one dyeing compound.

2. The method of claim 1, wherein:
    the at least one organosilicon compound is represented by formula (I):

    $$R_1R_2N\text{-}L\text{-}Si(OR_3)_a(R_4)_b \quad (I),$$

wherein:
    $R_1$ and $R_2$ represent, independently of one another, a hydrogen atom or a $C_1$-$C_6$ alkyl group,
    L represents a linear or branched, divalent $C_1$-$C_{20}$ alkylene group,
    $R_3$ and $R_4$ represent, independently of one another, a $C_1$-$C_6$ alkyl group,
    a represents an integer from 1 to 3, and
    b represents the integer 3−a; or
    the at least one organosilicon compound is represented by formula (II);

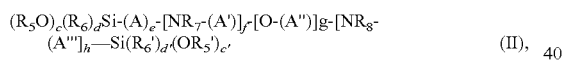
    $$(R_5O)_c(R_6)_dSi\text{-}(A)_e\text{-}[NR_7\text{-}(A')]_f\text{-}[O\text{-}(A'')]g\text{-}[NR_8\text{-}(A''')]_h\text{—}Si(R_6')_{d'}(OR_5')_{c'} \quad (II),$$

wherein:
    $R_5$, $R_5'$, $R_5''$, $R_6$, $R_6'$ and $R_6''$ represent, independently of one another, a $C_1$-$C_6$ alkyl group,
    A, A', A'', A''' and A'''' represent, independently of one another, a linear or branched, divalent $C_1$-$C_{20}$ alkylene group,
    $R_7$ and $R_8$ represent, independently of one another, a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group, or a group of formula (III):

$$\text{-}(A'''')\text{-}Si(R_6'')_{d''}(OR_5'')_{c''} \quad (III),$$

c represents an integer from 1 to 3,
    d represents the integer 3−c,
    c' represents an integer from 1 to 3,
    d' represents the integer 3−c',
    c'' represents an integer from 1 to 3,
    d'' represents the integer 3−c'',
    e represents 0 or 1,
    f represents 0 or 1,
    g represents 0 or 1,
    h represents 0 or 1, and
    at least one of e, f, g and h is different from 0.

3. The method of claim 2, wherein the at least one organosilicon compound is represented by formula (I):

    $$R_1R_2N\text{-}L\text{-}Si(OR_3)_a(R_4)_b \quad (I),$$

wherein;
    $R_1$ and $R_2$ both represent a hydrogen atom,
    L represents a linear, divalent $C_1$-$C_6$ alkylene group,
    $R_3$ and $R_4$ represent, independently of one another, a methyl group or an ethyl group,
    a represents the number 3, and
    b represents the number 0.

4. The method of claim 1, wherein the at least one organosilicon compound is selected from the group consisting of:
    (3-aminopropyl)triethoxysilane,
    (3-aminopropyl)trimethoxysilane,
    1-(3-aminopropyl)silanetriol,
    (2-aminoethyl)triethoxysilane,
    (2-aminoethyl)trimethoxysilane,
    1-(2-aminoethyl)silanetriol,
    (3-dimethylaminopropyl)triethoxysilane,
    (3-dimethylaminopropyl)trimethoxysilane,
    1-(3-dimethylaminopropyl)silanetriol,
    (2-dimethylaminoethyl)triethoxysilane,
    (2-dimethylaminoethyl)trimethoxysilane,
    1-(2-dimethylaminoethyl)silanetriol, and
    any combination thereof.

5. The method of claim 2, wherein the at least one organosilicon compound is represented by formula (II):

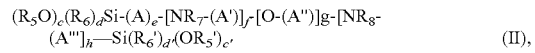
    $$(R_5O)_c(R_6)_dSi\text{-}(A)_e\text{-}[NR_7\text{-}(A')]_f\text{-}[O\text{-}(A'')]g\text{-}[NR_8\text{-}(A''')]_h\text{—}Si(R_6')_{d'}(OR_5')_{c'} \quad (II),$$

wherein;
    e and f both represent the number 1,
    g and h both represent the number 0,
    A and A' represent, independently of one another, a linear, divalent $C_1$-$C_6$ alkylene group, and
    $R_7$ represents a hydrogen atom, a methyl group, a 2-hydroxyethyl group, a 2-alkenyl group, a 2-aminoethyl group, or a group of formula (III).

6. The method of claim 1, wherein the at least one organosilicon compound is represented by formula (IV):

    $$R_9Si(OR_{10})_k(R_{11})_m \quad (IV),$$

wherein:
    $R_9$ represents a $C_1$-$C_{18}$ alkyl group,
    $R_{10}$ represents a hydrogen atom or a $C_1$-$C_6$ alkyl group,
    $R_{11}$ represents a $C_1$-$C_6$ alkyl group,
    k represents an integer from 1 to 3, and
    m represents the integer 3−k.

7. The method of claim 1, wherein the at least one organosilicon compound is selected from the group consisting of:
    methyltrimethoxysilane,
    methyltriethoxysilane,
    ethyltrimethoxysilane,
    ethyltriethoxysilane,
    propyltrimethoxysilane,
    propyltriethoxysilane,
    hexyltrimethoxysilane,
    hexyltriethoxysilane,
    octyltrimethoxysilane,
    octyltriethoxysilane,
    dodecyltrimethoxysilane,
    dodecyltriethoxysilane,
    octadecyltrimethoxysilane,
    octadecyltriethoxysilane, and
    any combination thereof.

8. The method of claim 1, wherein the second agent comprises at least two organosilicon compounds that are structurally different from one another.

9. The method of claim 1, wherein the sealing reagent comprises a compound selected from the group consisting of film-forming polymers, alkalizing agents, acidifying agents, and any combination thereof.

10. The method of claim 1, wherein the first agent further comprises an anionic surfactant.

11. The method of claim 1, wherein the first agent further comprises a nonionic surfactant.

12. The method of claim 1, wherein the first agent further comprises an amphoteric surfactant.

13. The method of claim 1, wherein the dyeing compound comprises an inorganic pigment selected from the group consisting of black iron oxide (CI 77499), yellow iron oxide (CI 77492), red iron oxide (CI 77491), and any combination thereof.

14. A multi-component packaging unit for dyeing keratinous material, the multi-component packaging unit comprising:
- a first container containing a first agent comprising hydrogen peroxide and water;
- a second container containing a second agent comprising at least one organosilicon compound selected from the group consisting of silanes having one, two, and three silicon atoms; and
- a third container containing a third agent comprising water and at least one dyeing compound; and
- a fourth container containing a fourth agent comprising at least one sealing reagent, wherein the first container, the second container, the third container, and the fourth container are packaged separately from one another.

15. A multi-component packaging unit for dyeing keratinous material, the multi-component packaging unit comprising:
- a first container containing a first agent comprising hydrogen peroxide and water;
- a second container containing a second agent comprising at least one organosilicon compound selected from the group consisting of silanes having one, two, and three silicon atoms;
- a third container containing a third agent comprising water;
- a fourth container containing a fourth agent comprising at least one dyeing compound; and
- a fifth container containing a fifth agent comprising at least one sealing reagent.

16. The method of claim 1, wherein the at least one dyeing compound comprises a pigment.

17. The method of claim 1, wherein the at least one dyeing compound comprises at least one anionic direct dye.

18. The method of claim 1, wherein the first agent further comprises a cationic surfactant.

19. The method of claim 1, wherein the hydrogen peroxide is present in an amount of from 0.5 to 12 wt %, based on the total weight of the first agent.

20. The method of claim 1, wherein the first agent further comprises an alkyl(poly)glucoside.

* * * * *